(12) United States Patent
Brubacher

(10) Patent No.: US 10,481,075 B2
(45) Date of Patent: Nov. 19, 2019

(54) MICROORGANISM EVALUATION SYSTEM

(71) Applicant: SoBru Solutions, Inc., Fullerton, CA (US)

(72) Inventor: John Miles Brubacher, La Mirada, CA (US)

(73) Assignee: SoBru Solutions, Inc., Fullerton, CA (US)

( * ) Notice: Subject to any disclaimer, the term of this patent is extended or adjusted under 35 U.S.C. 154(b) by 0 days.

(21) Appl. No.: 15/105,280

(22) PCT Filed: Dec. 15, 2014

(86) PCT No.: PCT/US2014/070420
§ 371 (c)(1),
(2) Date: Jun. 16, 2016

(87) PCT Pub. No.: WO2015/095085
PCT Pub. Date: Jun. 25, 2015

(65) Prior Publication Data
US 2016/0313230 A1    Oct. 27, 2016

Related U.S. Application Data

(60) Provisional application No. 61/916,343, filed on Dec. 16, 2013.

(51) Int. Cl.
*G01N 15/14* (2006.01)
*G01N 15/00* (2006.01)

(52) U.S. Cl.
CPC ......... *G01N 15/1459* (2013.01); *G01N 15/00* (2013.01); *G01N 2015/0003* (2013.01); *G01N 2015/0065* (2013.01)

(58) Field of Classification Search
CPC ........................... G01N 15/1459; G01N 15/00
(Continued)

(56) References Cited

U.S. PATENT DOCUMENTS 4,603,977 A * 8/1986 Bennett .................. G01N 21/51
356/436
5,713,303 A    2/1998 Willinsky et al.
(Continued)

FOREIGN PATENT DOCUMENTS

DE    10 2012 003 284 A1    8/2013
JP          4633672 B2    11/2007

OTHER PUBLICATIONS

Kim et al., Light-directed migration of D. discoideum slugs in microfabricated confinements, 2012, Sensors and Actuators (188), pp. 312-319.*

(Continued)

*Primary Examiner* — Kevin Joyner
*Assistant Examiner* — Holly M Mull
(74) *Attorney, Agent, or Firm* — Lodestone Legal Group; Jeromye V. Sartain

(57) ABSTRACT

A microorganism evaluation system comprising a viewing section for image acquisition, the viewing section comprising a viewing port configured to accommodate a fluid flow, at least one independently controlled imaging light source operably installed in the viewing section and configured to selectively illuminate the viewing port, and at least one independently controlled light stimulation device operably installed in the viewing section and configured to selectively emit light for invoking a motile response in a microorganism within the fluid flow in the viewing port, whereby the system synchronizes illumination of the at least one imaging light source and the at least one light stimulation device of the viewing section.

20 Claims, 19 Drawing Sheets

(58) Field of Classification Search
USPC .................................................. 435/288.3
See application file for complete search history.

(56) References Cited

U.S. PATENT DOCUMENTS

| | | | | |
|---|---|---|---|---|
| 2003/0155528 | A1* | 8/2003 | Tokuda | C12Q 1/04 250/461.2 |
| 2010/0007879 | A1* | 1/2010 | Mavliev | G01N 15/1459 356/336 |
| 2011/0242308 | A1* | 10/2011 | Igarashi | G01N 21/6458 348/79 |
| 2012/0118740 | A1* | 5/2012 | Garcia | B03C 5/005 204/547 |
| 2015/0140596 | A1* | 5/2015 | Mak | B01L 3/502761 435/29 |
| 2015/0198517 | A1* | 7/2015 | Simpson | G01N 15/1427 209/552 |
| 2015/0353981 | A1* | 12/2015 | Sim | C12Q 1/02 506/10 |

OTHER PUBLICATIONS

International Search Report and Written Opinion PCT/US2014/070420, dated Mar. 16, 2015.
Akiba, T. et al., "Design and Testing of an Underwater Microscope and Image Processing System of the study of Zooplankton Distribution," IEEE Journal of Oceanic Engineering, vol. 25, No. 1, pp. 97-104, Jan. 2000 (retrieved on Feb. 18, 2015).

\* cited by examiner

MICROORGANISM EVALUATION SYSTEM

RELATED APPLICATIONS

This application claims priority and is entitled to the filing date of U.S. Provisional application Ser. No. 61/916,343 filed Dec. 16, 2013, and entitled "Microorganism Evaluation System Viewing Section." The contents of the aforementioned application are incorporated herein by reference.

INCORPORATION BY REFERENCE

Applicant hereby incorporates herein by reference any and all patents and published patent applications cited or referred to in this application.

TECHNICAL FIELD

Aspects of this invention relate generally to evaluation systems, and more particularly to a microorganism evaluation system and a viewing section thereof configured for both stimulating and acquiring images of microorganisms within a fluid.

BACKGROUND ART

By way of background, a number of industries are affected by regulations relating to water treatment, such as ballast water treatment systems ("BWTS") on ships and the like. Such regulations require that microorganisms be effectively treated (killed) by the BWTS before such water is returned to the ocean or other body of water. Generally speaking, Zooplankton in the size range of approximately 10 to 50 microns is an "indicator" microorganism used to determine the effectiveness of treatment, though it will be appreciated that other organisms in alternative size ranges are possible depending on the context and other factors, such that organisms greater than 50 microns may also be the "indicators." In the art, monitoring of the effectiveness of such BWTS has largely been handled through samples submitted to a lab, there most often involving human examination under a microscope. Such approaches to compliance assessment have numerous shortcomings in terms of accuracy, speed, and cost. Similarly, flow cytometry systems, though typically offering relatively higher throughput, are also lacking in terms of viability determination (determinations regarding whether an organism is living) and portability for field or deployed uses. Applicant has already made improvements over such prior art systems by developing new and novel evaluation systems for determining whether microorganisms are living, such as disclosed in pending international patent application Ser. No. PCT/US13/46334 filed Jun. 18, 2013, and U.S. provisional patent application Ser. No. 61/661,011 filed Jun. 18, 2012, to which the international application claims priority, both entitled "Microorganism Evaluation System." The contents of the aforementioned applications are incorporated herein by reference.

DISCLOSURE OF INVENTION

Aspects of the present invention teach certain benefits in construction and use which give rise to the exemplary advantages described below.

The present invention solves the problems described above by providing new and novel improvements in or relating to the viewing section of such microorganism evaluation systems wherein image data relating to organisms within a fluid flow is acquired and, in various embodiments, further stimulation of the organisms is provided for purposes of triggering a motile response of the organisms that is then detected and captured by the imaging equipment, as discussed in detail below.

A primary objective inherent in the above described system and method of use is to provide advantages not taught by the prior art.

Another objective is to provide a microorganism evaluation system comprising a viewing section for image acquisition, the viewing section comprising: a viewing port configured to accommodate a fluid flow from a viewing section body inlet to a viewing section body outlet; at least one independently controlled imaging light source operably installed in the viewing section and configured to selectively illuminate the viewing port; and at least one independently controlled light stimulation device operably installed in the viewing section and configured to selectively emit light for invoking a motile response in a microorganism within the fluid flow in the viewing port, whereby the system synchronizes illumination of the at least one imaging light source and the at least one light stimulation device of the viewing section.

Another objective is to provide such a microorganism evaluation system wherein the at least one imaging light source is installed in the viewing section so as to provide substantially side illumination within the viewing port.

Another objective is to provide such a microorganism evaluation system having one or more further alternative organism stimulation mechanisms incorporated on, in, or adjacent to the viewing section.

Another objective is to provide a method of operating the viewing section of the microorganism evaluation system, comprising the steps of: activating the independently controlled imaging light source operably installed in the viewing section and configured to selectively illuminate the viewing port thereof, the viewing port configured to accommodate a fluid flow; and activating the independently controlled light stimulation device operably installed in the viewing section and configured to selectively emit light for invoking a motile response in a microorganism within the fluid flow in the viewing port.

It will be appreciated by those skilled in the art that the exact configuration of the apparatus may take a number of forms to suit particular applications without departing from the spirit and scope of the present invention. Accordingly, it will be further appreciated that the configuration of the apparatus shown and described is exemplary and that the invention is not so limited.

Other features and advantages of aspects of the present invention will become apparent from the following more detailed description, taken in conjunction with the accompanying drawings, which illustrate, by way of example, the principles of aspects of the invention.

BRIEF DESCRIPTION OF DRAWINGS

The accompanying drawings illustrate aspects of the present invention. In such drawings.

Figure 1:
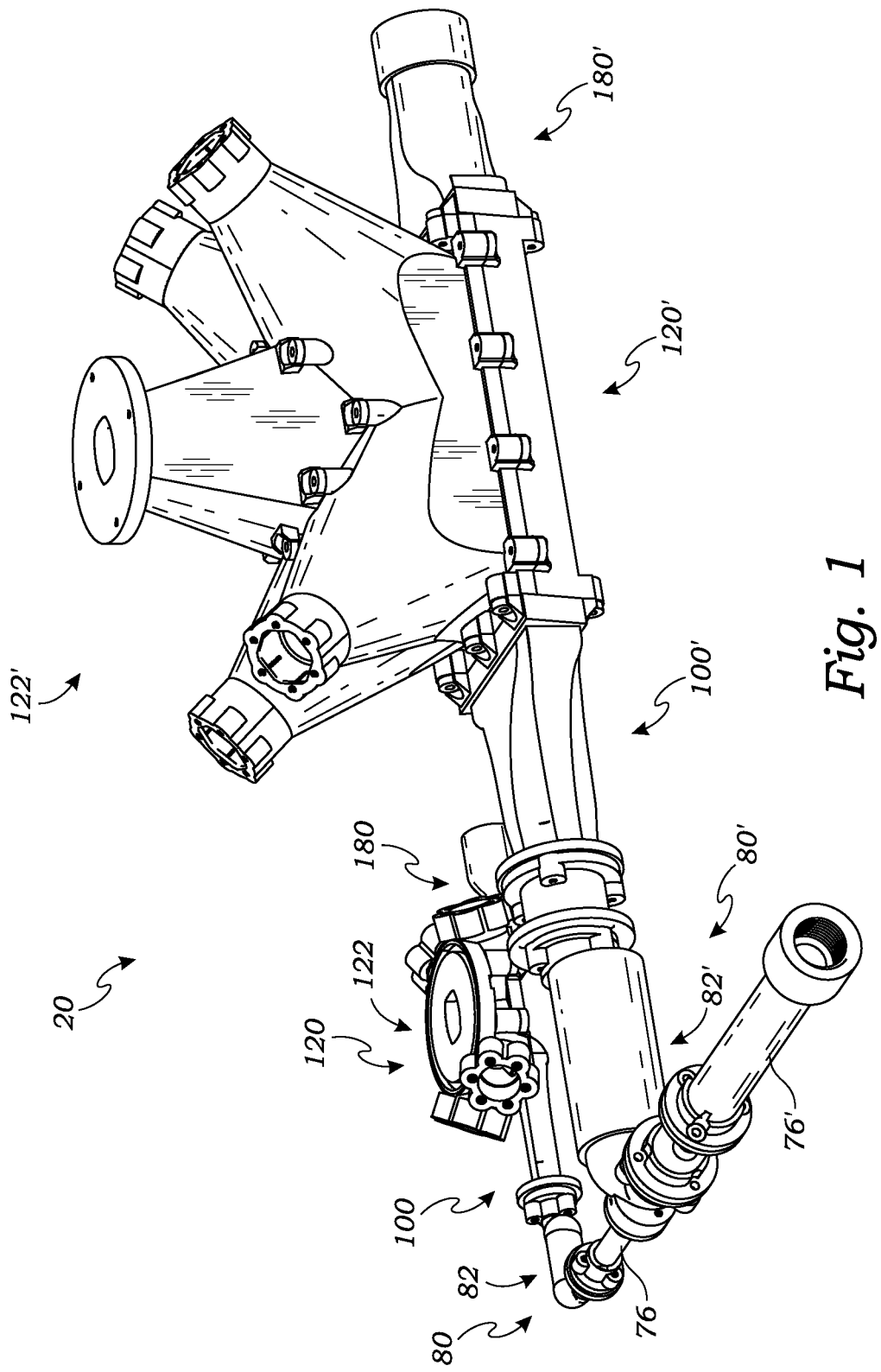
FIG. 1 is a perspective view of an operative portion of an exemplary microorganism evaluation system, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

MODES FOR CARRYING OUT THE INVENTION

The above described drawing figures illustrate aspects of the invention in at least one of its exemplary embodiments, which are further defined in detail in the following description.

As an overview, and with reference to the perspective view of FIG. 1, the exemplary sample acquisition system 20 has four main hardware components or sections, which are discussed in turn below, with the focus herein being on being on the third: (1) a microorganism stimulation section 80; (2) a flow normalizing section 100; (3) a viewing section 120; and (4) an outlet section 180. As shown, there may be one such arrangement or two or more, more about which is said below. There are or may also be related tanks, tubes, filters, pumps, and other aspects, whether or not shown, that may facilitate the collection and processing of a fluid sample according to aspects of the invention, which could be necessary in particular contexts but are nevertheless ancillary components that can be substituted for by other equivalent structure now known or later developed and so are not the focus of the present invention. It will be appreciated by those skilled in the art that the exact configuration of the system and its four main sections or features, again in any number and whether in parallel or in series, may take a number of forms to suit particular applications without departing from the spirit and scope of the present invention. Accordingly, it will be further appreciated that the configurations of the system shown and described are exemplary and that the invention is not so limited.

Figure 14:
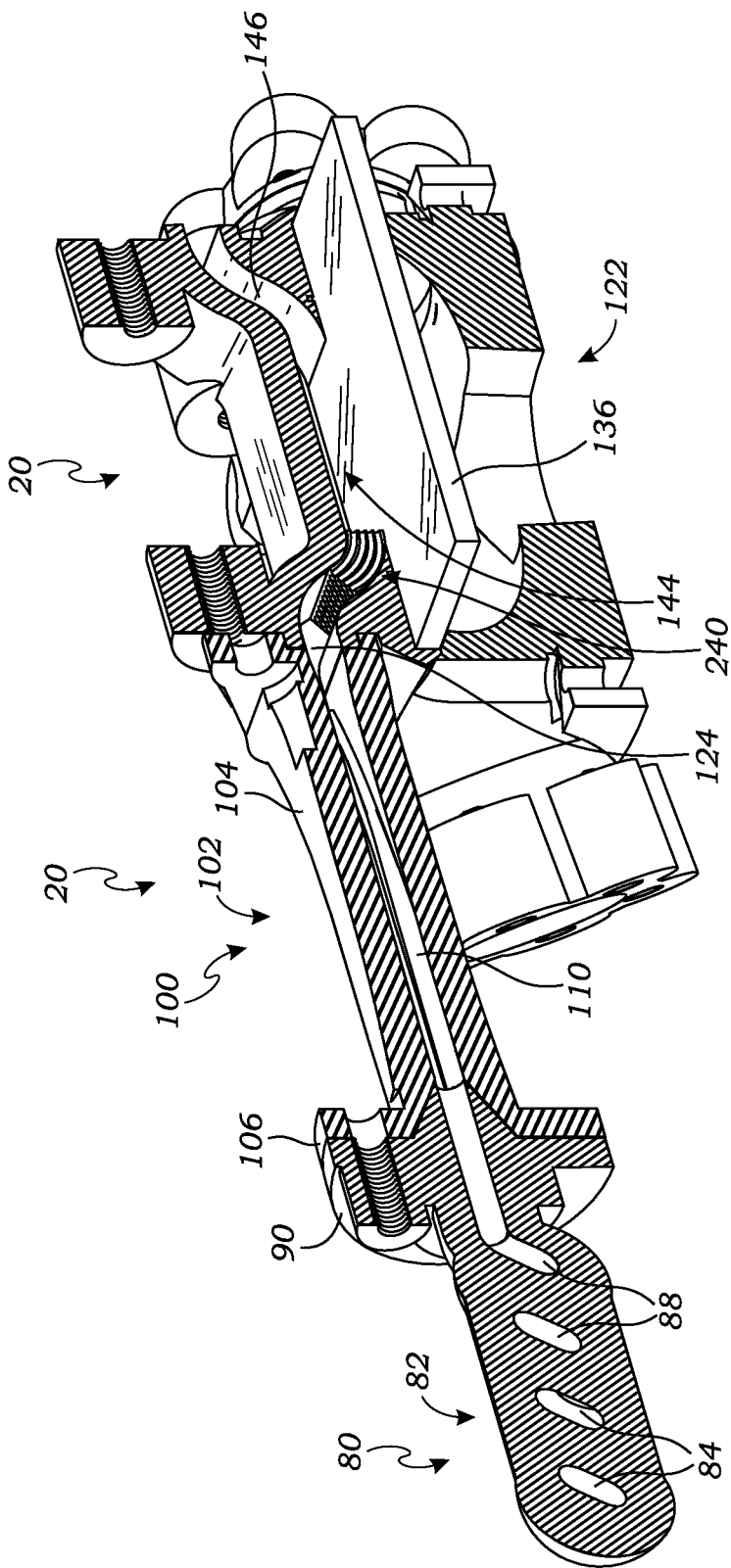
FIG. 14 is a further partial sectional view of the exemplary viewing section of FIG. 12.

Turning now to FIG. 1, there is shown a perspective view of an operative portion of an exemplary microorganism evaluation system 20 according to aspects of the present invention. Fundamentally, it will be appreciated that in the exemplary embodiment of fluid flow sampling, the disclosed evaluation system 20 is directed to or embodies a method by which such a fluid flow is first acted on or subjected to some sort of input in order to stimulate or induce a motile response from living microorganisms within the flow, and then to visually observe and acquire image data relative to such a motile response for the purpose of determining whether any organisms within the fluid sample are living. The system 20 comprises, in the exemplary embodiment, a first or primary, relatively larger microorganism stimulation section 80' defining a disorientation spiral 82' fed by tubing 76' via coupling 86' that is itself sampled by a secondary, relatively smaller microorganism stimulation section 80 defining a disorientation spiral 82 fed by tubing 76 via coupling 86, such sampling being as by isokinetic sampling, for example. Though not shown in the present application, except for the sectional view of FIG. 14 showing the secondary microorganism stimulation section 80 in one illustrative embodiment, it will be appreciated based on the applications incorporated by reference herein that within each of the stimulation sections 80, 80' there may be formed a disorientation spiral or helical flow path configured to induce the fluid in the spiral to rotate around the tubular or helical axis, which will stimulate (agitate) the inertial sensing mechanisms found within the microorganisms. Thus, the previously disclosed inertial stimulation sections 80, 80' are one example of a means by which to induce a motile response within a living organism. Herein are disclosed at least six other such means or improvements thereto, each of which is itself exemplary and which it will be appreciated may be employed alone or in various combinations depending on the context, such that any particular combination of stimulation means illustrated herein is merely exemplary of features and aspects of the invention and expressly non-limiting.

Figure 2:
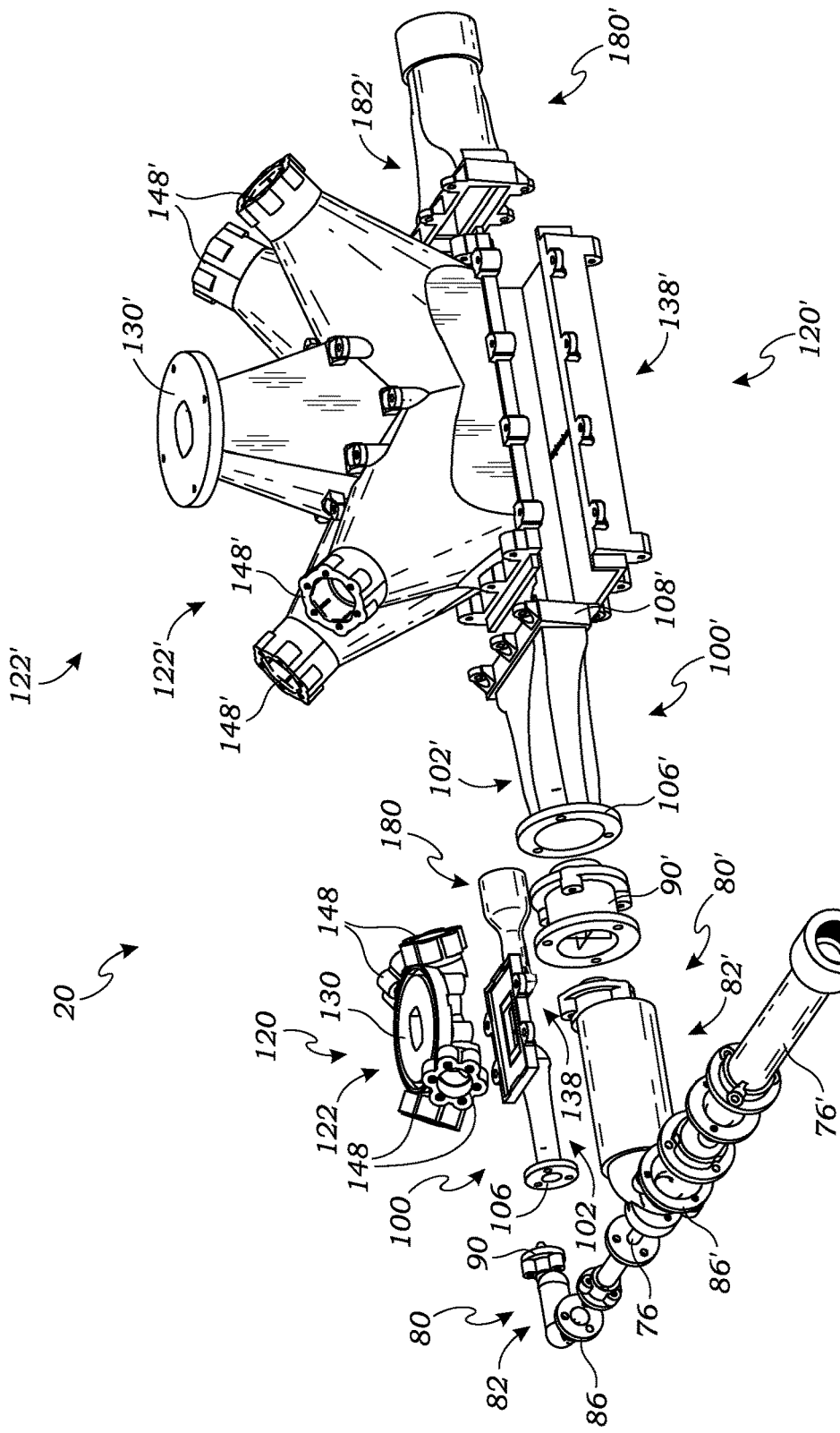
FIG. 2 is an exploded perspective view thereof, in accordance with at least one embodiment.
Figure 3:
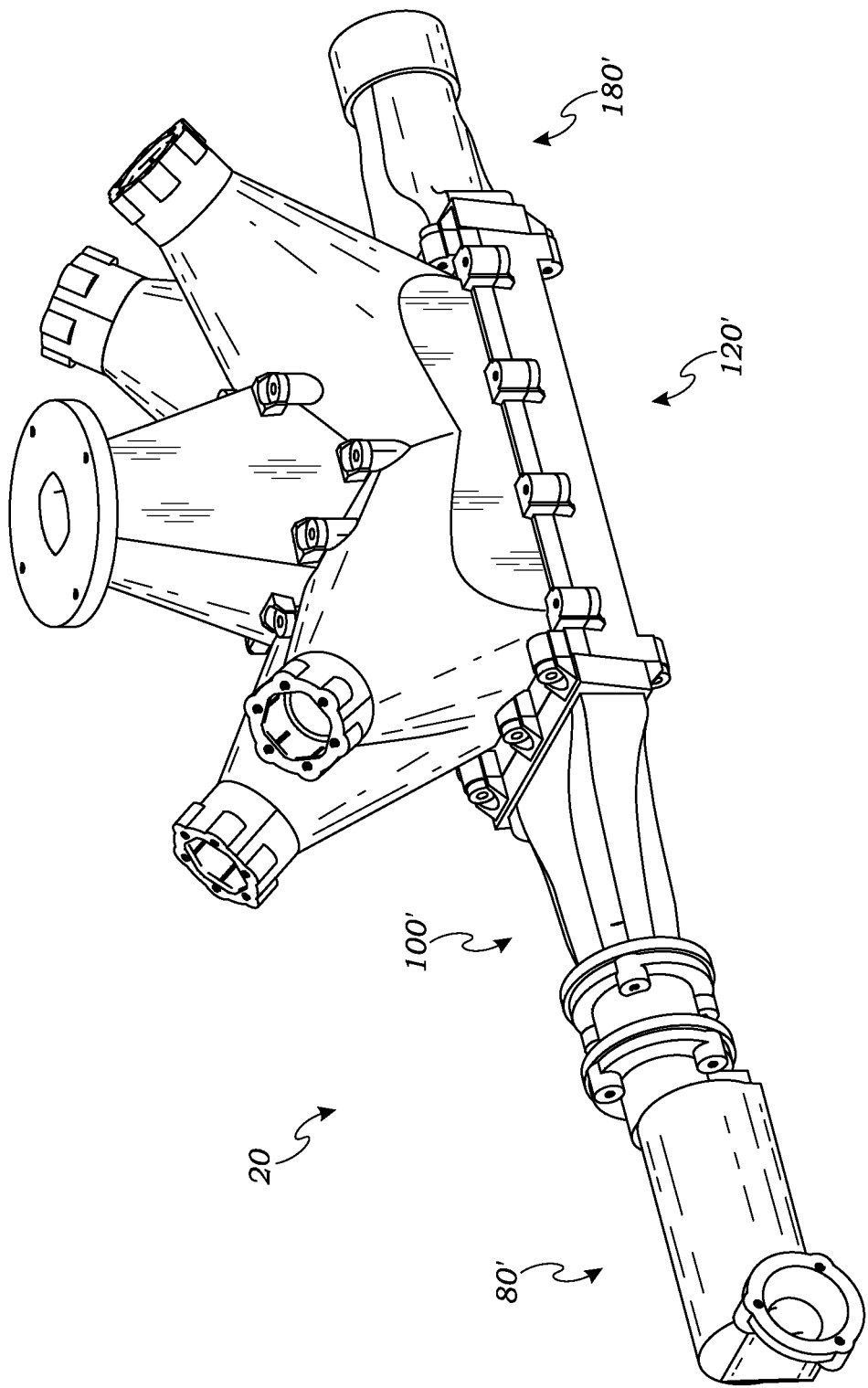
FIG. 3 is an enlarged partial perspective view of a first exemplary viewing section thereof, in accordance with at least one embodiment.
Figure 4:
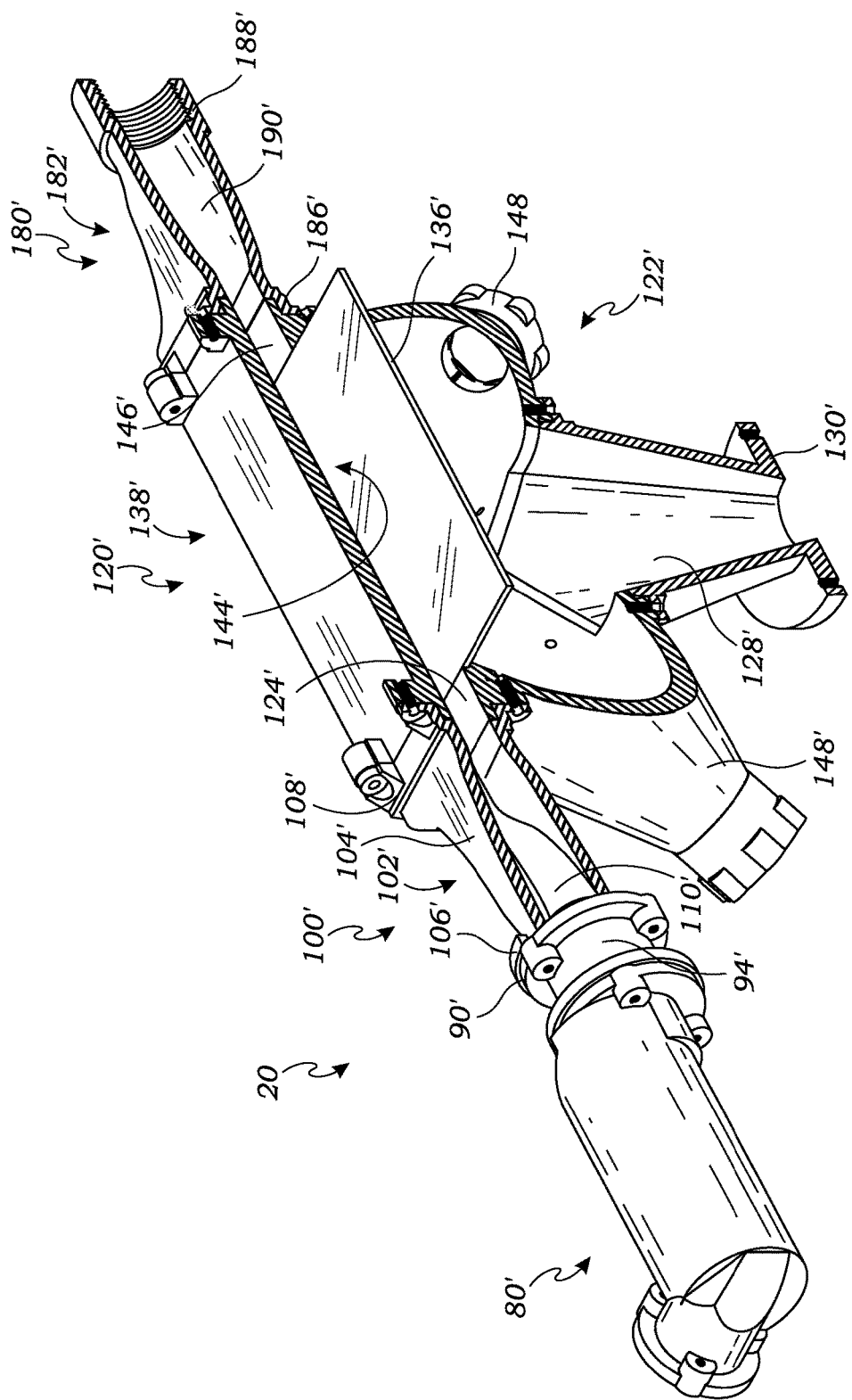
FIG. 4 is a partial sectional view of the exemplary viewing section of FIG. 3 taken from a first perspective.
Figure 5:
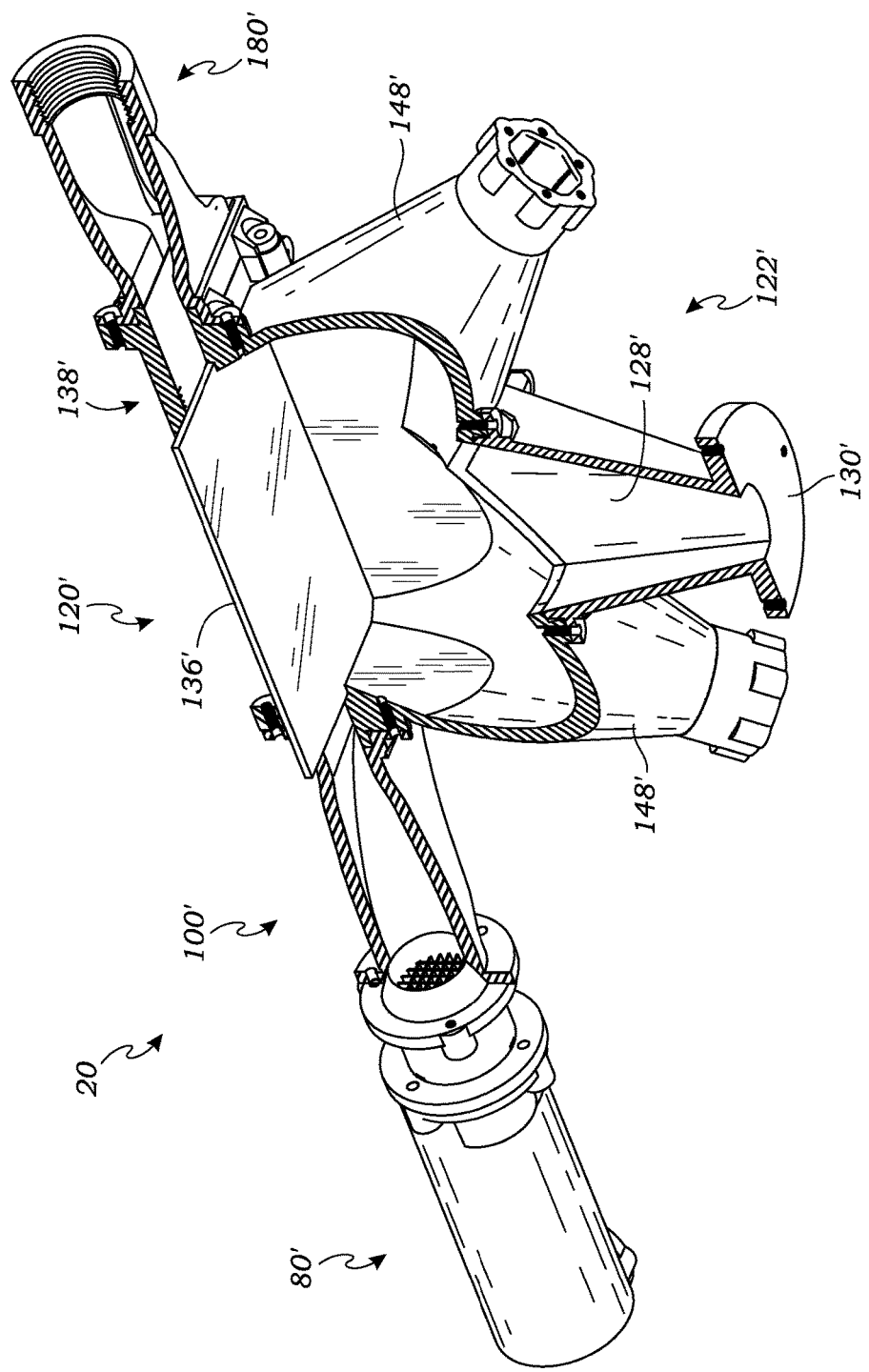
FIG. 5 is a further partial sectional view of the exemplary viewing section of FIG. 3 taken from a second perspective.
Figure 6:
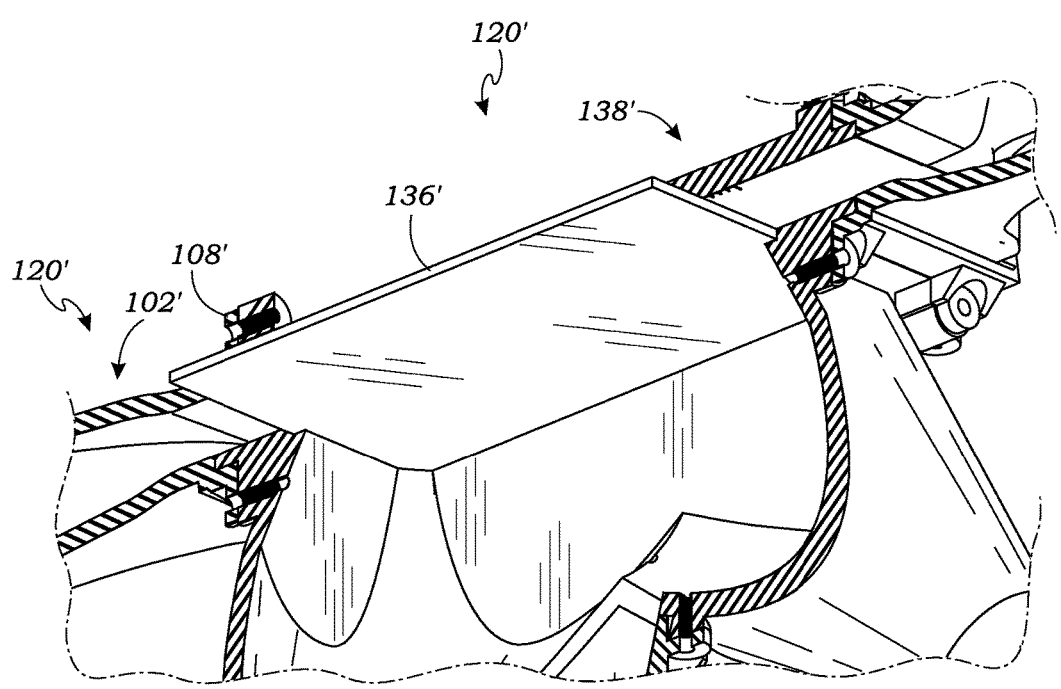
FIG. 6 is an enlarged partial sectional view of the exemplary viewing section of FIG. 3.
Figure 7:
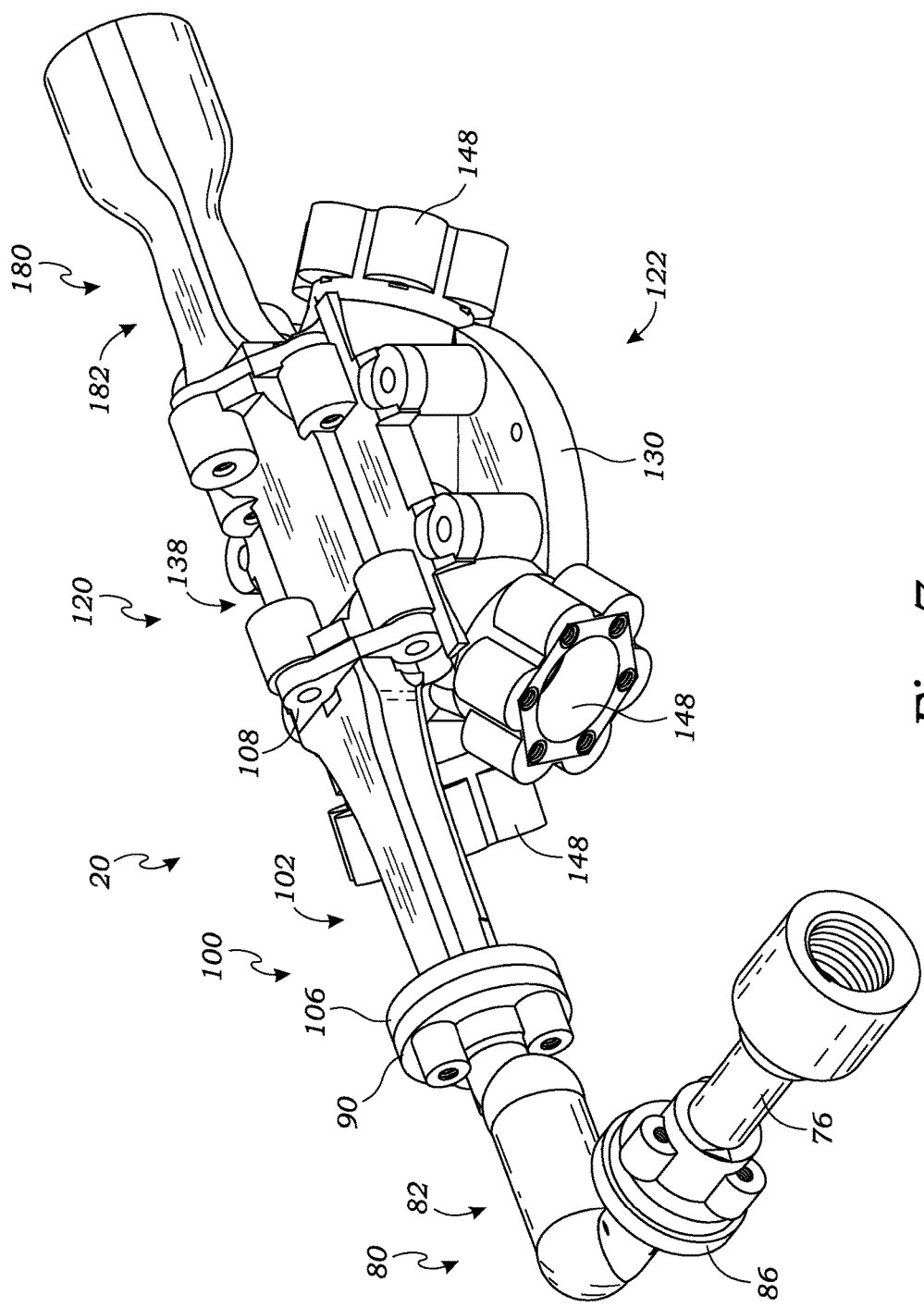
FIG. 7 is an enlarged partial perspective view of a second exemplary viewing section thereof, in accordance with at least one embodiment.
Figure 8:
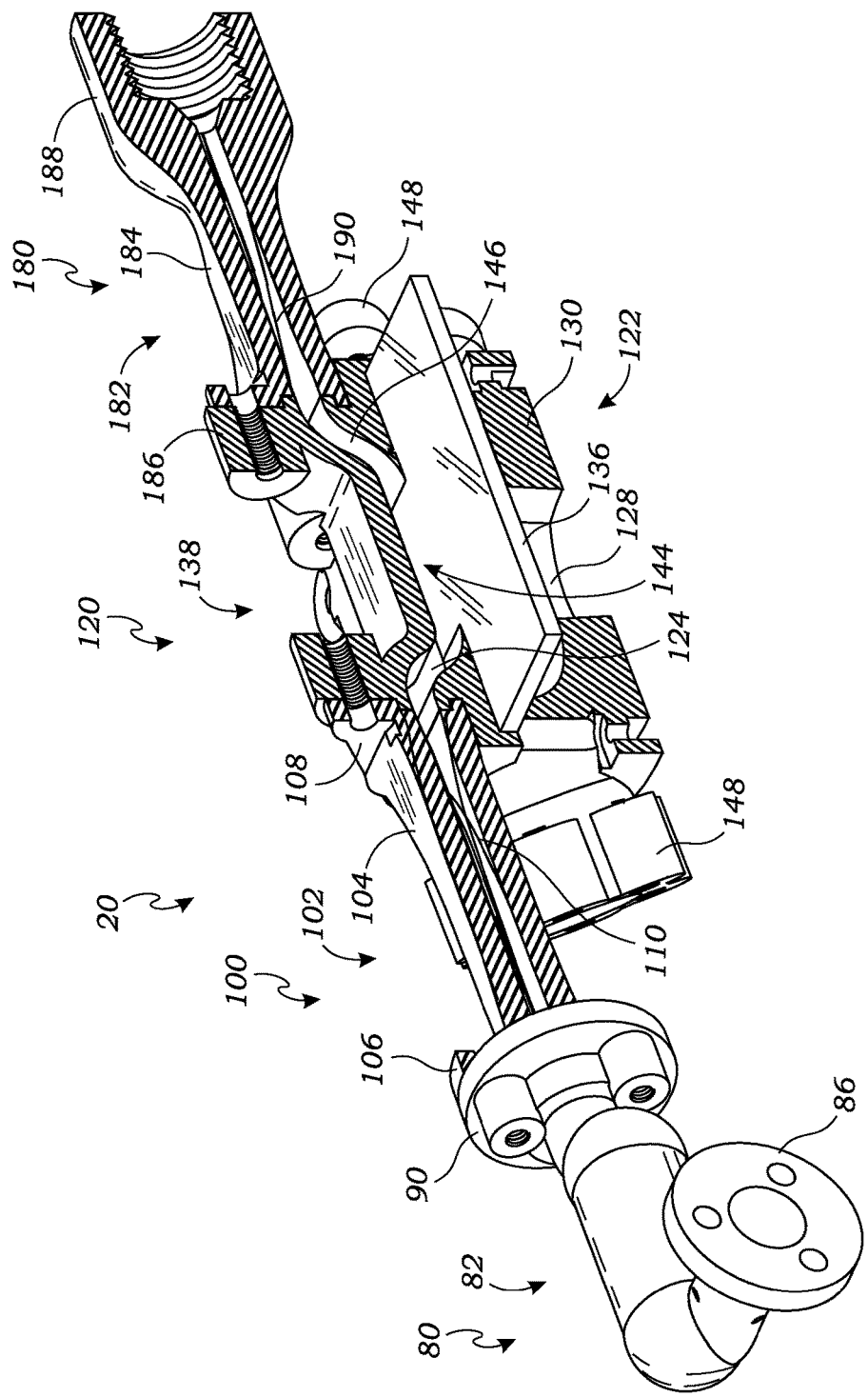
FIG. 8 is a partial sectional view of the exemplary viewing section of FIG. 7 taken from a first perspective.
Figure 9:
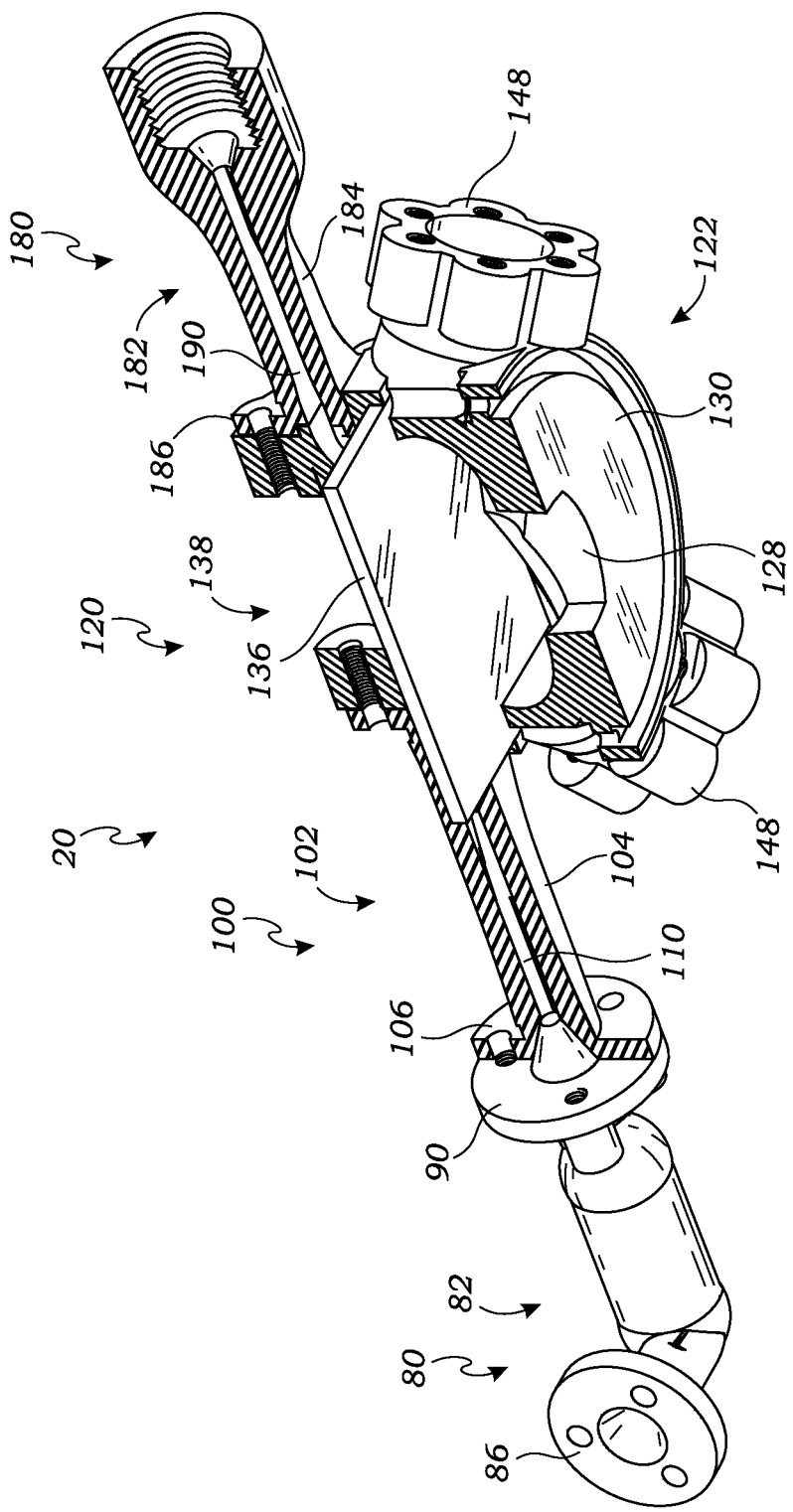
FIG. 9 is a further partial sectional view of the exemplary viewing section of FIG. 7 taken from a second perspective.
Figure 10:
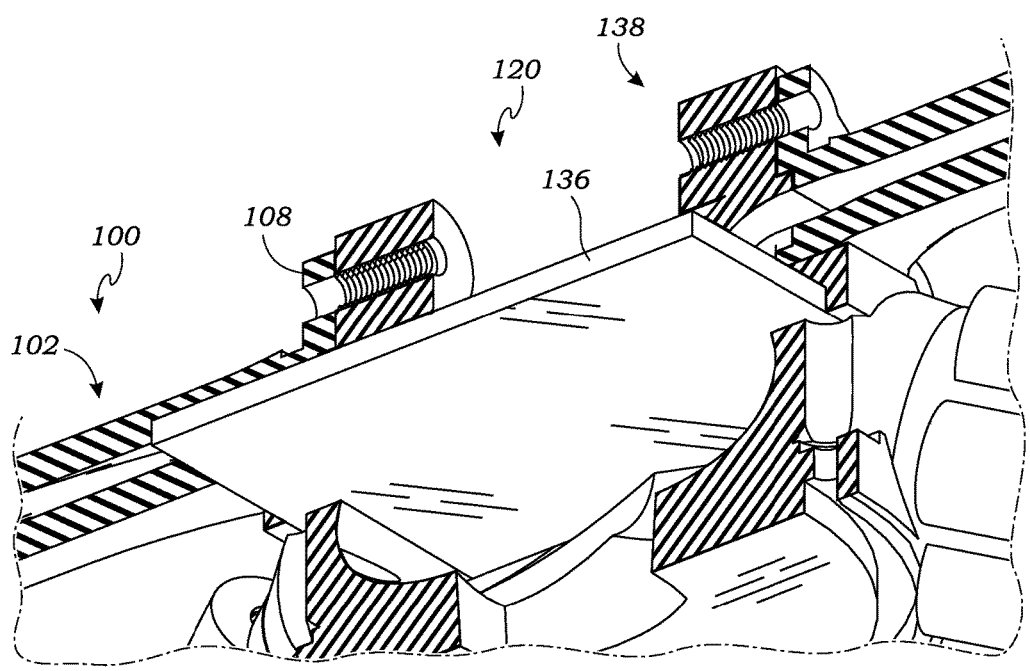
FIG. 10 is an enlarged partial sectional view of the exemplary viewing section of FIG. 7.

With continued reference to FIG. 1 and further with reference to the exploded perspective view of FIG. 2, within the off-line sampling portion of the evaluation system 20, from the smaller inertial stimulation section 80 the flow proceeds to the flow normalizing section 100 defining an inlet chute 102, such components being joined via coupling 90 of the stimulation section 80 and coupling 106 of the flow normalizing section 100. From the flow normalizing section 100, the flow continues into the viewing section 120. Similarly, in the main fluid flow, from the larger inertial stimulation section 80' the flow proceeds to the flow normalizing section 100' defining an inlet chute 102', such components being joined via coupling 90' of the stimulation section 80' and coupling 106' of the normalizing section 100', and from the flow normalizing section 100' into the viewing section 120'. Much more will be said about the viewing sections 120, 120' below, as that is the primary region of the exemplary microorganism evaluation system 20 wherein the various new and novel stimulation means and related improvements are or may be employed as set forth herein. Generally, as shown, each viewing section 120, 120' comprises in the exemplary embodiment a viewing section body 122, 122' having an optical system mount 130, 130' and one or more illumination ports 148, 148', and an opposite back plate 138, 138' for completing and enclosing the viewing section 120, 120' inner space that defines the viewing port 144, 144' of each (FIGS. 4 and 8). As a threshold matter, it is to be understood that the illustrated hardware components—here essentially the microorganism stimulation section 80, 80', the flow normalizing section 100, 100', and the viewing section 120, 120', as well as the outlet section 180, 180' leading away from the viewing section 120, 120'—are merely representative or illustrative of aspects of the invention and are not limiting, whether in configuration or arrangement. Simply for illustration regarding scale in the exemplary embodiment, the larger stimulation section 80' helical flow path may have an inside diameter of approximately 13 mm feeding into a viewing section 120' that is nominally 56.25 mm wide by 12 mm high, as compared to the smaller sampling portion in which the stimulation section 80 may have a nominal inside diameter of 2.4 mm and a viewing section 120 that is nominally 11.25 mm wide by 3 mm high. The resulting dual system 20 enables more throughput for use in contexts where larger volumetric or real-time sampling is desired as well as potentially enabling higher accuracy by secondary line sampling and evaluation within a viewing section 120 that has a nominal 3 mm depth of field while still allowing an acceptable aggregate throughput by employing the primary line having a nominal 12 mm depth of field, or a cross-sectional area of 675 mm$^2$ versus the 33.75 mm$^2$ of the secondary sampling line. It will once again be appreciated that such features may be combined in a variety of ways and employ a variety of sizes, shapes, and technologies now known or later developed without departing from the spirit and scope of the invention.

Referring now to FIGS. 3-6, there are shown enlarged partial perspective and sectional views of the primary, relatively larger line of the exemplary dual sampling microorganism evaluation system 20 generally comprising the stimulation section 80', the flow normalizing section 100', the viewing section 120', and the outlet section 180'. As shown particularly in FIGS. 4 and 5, in a reverse orientation relative to FIGS. 1-3, the flow normalizing section 100' generally comprises the inlet chute 102'. It is noted that while a section of tubing 94' is shown as interconnecting the stimulation section 80' and the flow normalizing section 100', or effectively defining he coupling 90', this is not necessary, and the two sections 80', 100' may instead be connected directly—it will be appreciated that any such connectivity of the respective parts of the system 20 is possible in the present invention without departing from its spirit and scope. The chute 102' again has at its proximal end the inlet chute first coupling 106' configured to connect to the stimulation section coupling 90' and further has at is distal end an inlet chute second coupling 108' configured for connecting the inlet chute 102' to the viewing section body 122' and the back plate 138'. Once more, though a particular form and geometry of the inlet chute second coupling 108' is shown, here in the form of a plate substantially perpendicular to the axis of the inlet chute 102' and having holes formed for the assembly thereof as by bolts or screws to the respective parts of the viewing section 120', the invention is not so limited. More notably, it can be seen that the exemplary inlet chute 102' has an inlet chute body 104' in which is formed an inlet chute inner bore 110' along its entire length, which bore 110' is substantially tapered or expanding from the entrance to the inlet chute 102' at the end adjacent the inlet chute first coupling 106' to the exit from the inlet chute 102' adjacent the inlet chute second coupling 108'. Briefly regarding the outlet section 180' defined by an outlet chute 182' that effectively takes the sample flow away from the viewing section 120' in much the same way, but in reverse, as the inlet chute 102' delivers the sample flow to the viewing section 120', it can be seen that the outlet chute inner bore 190' tapers inwardly or contracts from the entrance to the outlet chute 182' at the end adjacent the outlet chute first coupling 186' that is connected to the viewing section body 122' and back plate 138' to the exit from the outlet chute 182' adjacent the outlet chute second coupling 188' that is configured to connect to other downstream components of the system 20. Again, those skilled in the art will appreciate that all such sizes and shapes and configurations of such inlet and outlet components, generally directed to slowing the fluid flow as it enters the viewing section 120' and to speeding up the fluid flow as it leaves the viewing section 120', are possible in the present invention without departing from its spirit and scope.

As best seen in FIG. 4, the exemplary viewing section 120' is shown with the viewing section body 122' upside down and in section along its length or flow throughput axis. The body 122' effectively has a viewing section body inlet 124' coinciding with the distal end of the inlet chute 102' at its second coupling 108' and a viewing section body outlet 146' coinciding with the proximal end of the outlet chute 182' at its first coupling 186'. Three sides of the actual viewing port 144' or the true flow path through the viewing section 120' are formed by the inside bottom and side surfaces of the back plate 138' that installs onto the viewing section body 122' substantially opposite the optical system mount 130' and related cavity opening 128' for allowing viewing into and of the viewing port 144' by optical equipment (not shown) installed on the mount 130'. Opposite of or spaced from and substantially parallel to the back plate 138' there is positioned a clear or substantially transparent viewing plate 136' (not shown in section or as transparent) offset from the cavity opening 128', the viewing plate 136' seating within the viewing section body 122' so as to form the fourth side of the viewing port 144' through which the fluid sample flows and is visually inspected and image data relating thereto is acquired as discussed in more detail below. With continued reference to FIGS. 3-6, there is also shown multiple illumination ports 148' intersecting the viewing section body 122', in each of which there may be installed imaging LEDs or the like so as to illuminate particularly the viewing port 144, more about which will also be said below. Again, any number and configuration of such illumination ports 148' and any lighting units now known or later developed may be incorporated into the viewing section 120' without departing from the spirit and scope of the present invention.

Referring now to FIGS. 7-10, there are shown enlarged partial perspective and sectional views of the secondary, relatively smaller line of the exemplary dual sampling microorganism evaluation system 20 that samples from the main line shown in FIGS. 3-6, again generally comprising the stimulation section 80, the flow normalizing section 100, the viewing section 120, and the outlet section 180, here in a reverse orientation relative to FIGS. 1 and 2, except that the stimulation section 80 and related feed pipe 76 are in substantially the same orientation. As shown particularly in FIGS. 8 and 9, the flow normalizing section 100 generally comprises the inlet chute 102 again having at its proximal end the inlet chute first coupling 106 configured to connect to the stimulation section coupling 90 and further having at is distal end an inlet chute second coupling 108 configured for connecting the inlet chute 102 to the viewing section body 122 and the back plate 138. Once more, though a particular form and geometry of the inlet chute second coupling 108 is shown, here in the form of a plate substantially perpendicular to the axis of the inlet chute 102 and having holes formed for the assembly thereof as by bolts or screws to the respective parts of the viewing section 120, the invention is not so limited. More notably, it can be seen that the exemplary inlet chute 102 has an inlet chute body 104 in which is formed an inlet chute inner bore 110 along its entire length, which bore 110 is once again substantially tapered or expanding from the entrance to the inlet chute 102 at the end adjacent the inlet chute first coupling 106 to the exit from the inlet chute 102 adjacent the inlet chute second coupling 108. Briefly regarding the outlet section 180 defined by an outlet chute 182 that effectively takes the sample flow away from the viewing section 120 in much the same way, but in reverse, as the inlet chute 102 delivers the sample flow to the viewing section 120, it can be seen that the outlet chute inner bore 190 tapers inwardly or contracts from the entrance to the outlet chute 182 at the end adjacent the outlet chute first coupling 186 that is connected to the viewing section body 122 and back plate 138 to the exit from the outlet chute 182 adjacent the outlet chute second coupling 188 that is configured to connect to other downstream components of the system 20. Again, those skilled in the art will appreciate that all such sizes and shapes and configurations of such inlet and outlet components, generally directed to slowing the fluid flow as it enters the viewing section 120 and to speeding up the fluid flow as it leaves the viewing section 120, are possible in the present invention without departing from its spirit and scope. It is further noted in the exemplary embodiment of the viewing section 120 of FIGS. 7-10 that the flow path leading into and out of the viewing section 120, and particularly the viewing port 144, curves down and back up again, more about which is said below; such geometrical details are expressly non-limiting and may simply be a function of spatial constraints, desired depth of field, or other considerations in a particular context.

As best seen in FIG. 8, the exemplary viewing section 120 is shown with the viewing section body 122 upside down relative to FIGS. 1 and 2 and in section along its length or flow throughput axis. The body 122 effectively has a viewing section body inlet 124 coinciding with the distal end of the inlet chute 102 at its second coupling 108 and a viewing section body outlet 146 coinciding with the proximal end of the outlet chute 182 at its first coupling 186. Three sides of the actual viewing port 144 or the true flow path through the viewing section 120 are formed by the inside bottom and side surfaces of the back plate 138 that installs onto the viewing section body 122 substantially opposite the optical system mount 130 and related cavity opening 128 for allowing viewing into and of the viewing port 144 by optical equipment (not shown) installed on the mount 130. Opposite of or spaced from and substantially parallel to the back plate 138 there is positioned a clear or substantially transparent viewing plate 136 (again not shown in section or as transparent) offset from the cavity opening 128, the viewing plate 136 seating within the viewing section body 122 so as to form the fourth side of the viewing port 144 through which the fluid sample flows and is visually inspected and image data relating thereto is acquired as discussed in more detail below. With continued reference to FIGS. 7-10, there is also shown multiple illumination ports 148 intersecting the viewing section body 122, in each of which there may be installed imaging LEDs or the like so as to illuminate particularly the viewing port 144, more about which will also be said below. Again, any number and configuration of such illumination ports 148 and any lighting units now known or later developed may be incorporated into the viewing section 120 without departing from the spirit and scope of the present invention. For example, and without limitation, in connection with any such viewing section 120, 120' there may be more or less than the four illumination ports illustrated in the exemplary embodiments, and each port may be taller or shorter than the ports shown depending on the focal length of or diffusion from the associated imaging LED or other light source in each port as well as other geometrical considerations. Furthermore, in alternative arrangements the illumination ports may be considerably reduced in size and incorporated into the side walls of the viewing section as illustrated in the alternative exemplary embodiment of FIGS. 17-19, discussed below.

Figure 11:
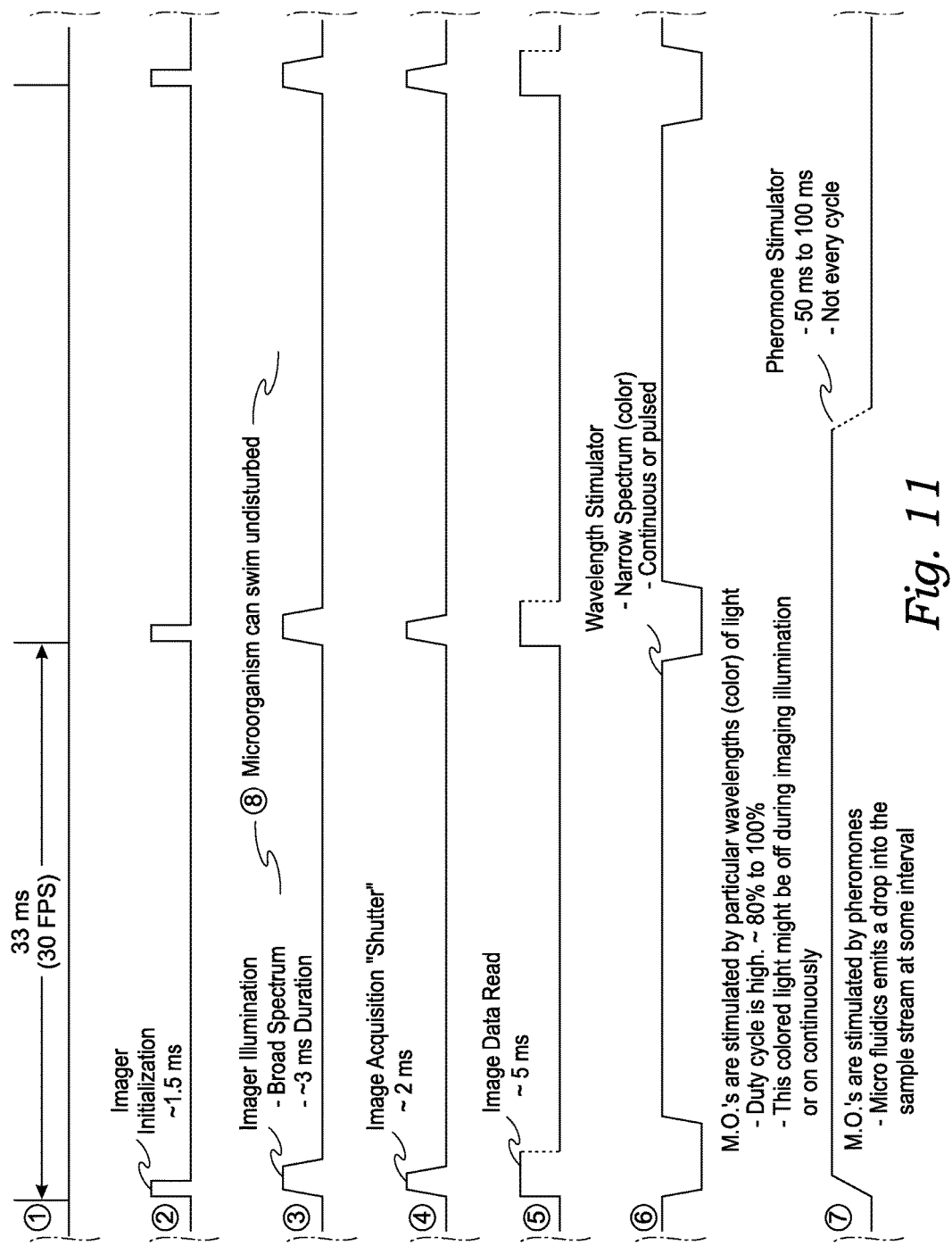
FIG. 11 is a timing diagram thereof, in accordance with at least one embodiment.

Turning now to FIG. 11, there is shown a timing diagram relative to essentially the viewing section 120 (FIGS. 1-10), such as those disclosed herein or in the prior patent applications incorporated herein by reference, and particularly to the timing within the viewing section 120 of the imager illumination and image acquisition or "shutter" events relative to other lighting or stimulation events, with an objective being to synchronize illumination with image capture to allow for various forms of organism stimulation without interference from imaging requirements. That is, it is desirable that the image illumination and capture events be effectively synchronized and independently controlled relative to other stimulation events within the viewing section 120, particularly if those events also involve light, though it will be appreciated by those skilled in the art that in some circumstances such synchronization will not be necessary or desirable, such as for example a scenario wherein there is no light-based stimulation or wherein stimulation light does not interfere with or adversely affect illumination light and image acquisition. In the exemplary smaller viewing section 120, the size of the viewing port 144 as noted above is approximately 11.25 mm wide by 20 mm long, setting then a viewing port volume (W×L×H) of approximately 225 mm$^3$ (11.25 mm×20 mm×3 mm) with a nominal 3 mm depth of field. Though system flow rates can vary widely based on a number of factors, the time for the flow, or a particular organism, to pass through the viewing section 120 is approximately on the order of one to ten (1-10) seconds. What this translates to, if a substantial number of image captures of the same organism are to be obtained (e.g., on the order of 25-250 or greater discrete images) on which computational analysis is to be performed in determining organism-generated movement and thus life, is a cycle time of approximately 33 ms based on 30 FPS (frames per second), or more generally in the range of approximately fifteen to forty-five milliseconds (15-45 ms). As shown in the timing diagram, then, within a representative viewing section 120 and based on current imaging technology and equipment and the exemplary throughput and other characteristics noted, what is represented is the timing of various events relative to each other within the exemplary 30 FPS cycle. Those skilled in the art will appreciate that the "frames per second" capability of the imaging equipment and thus the cycle time, the flow rate, the geometry of the viewing section 120, and a number of other such factors all may be changed to suit particular applications and to accommodate any related technologies now known or later developed in the art, such that the timing diagram is to be understood as merely illustrative of features and aspects of the present invention and non-limiting. That is, it will be appreciated that as imaging technology improves and 60, 120, or more FPS image acquisition is achievable, the dwell times within the viewing section 120 can be reduced accordingly while still being able to obtain the desired number of discrete images or data points per organism moving with the flow through the viewing section. Relatedly, variables such as the ability and timing to turn on and off, or strobe, the illumination lighting, as discussed further below, and the typical stimulation response times of the organisms being evaluated or used as the "indicators" are also factors in establishing the throughput of the viewing section 120 relative to the data to be captured. Accordingly, the evaluation system and particularly the viewing section design according to aspects of the present invention can be "tuned" as desired to suit particular applications—where relatively greater accuracy and/or lower cost are a priority or the organisms are relatively slower moving or responding, longer dwell times may be desired and obtained, even beyond the exemplary 10 seconds, by making the viewing section relatively larger or simply slowing down the flow rate through the system, for example, in which case relatively lower FPS imaging equipment and/or relatively slower toggling illumination light sources may be employed at reduced cost. Or, if relatively higher throughput is desired instead of or in addition to accuracy or is simply possible due to relatively fast indicator organism response rates, relatively higher FPS imaging equipment can be used and/or relatively smaller viewing section geometry, such as in cases where the "package" size is also an important factor. Those skilled in the art will ultimately appreciate that a number of such variables are interrelated and thus that a wide variety of system configurations are possible according to aspects of the present invention without departing from its spirit and scope. Moreover, it will be appreciated that even the exemplary diagram based on 30 FPS contains certain assumptions and "best guesses" about the performance or capability of some of the equipment, such that the diagram is not to be taken literally or "to scale," but is instead intended to simply convey the overall concept of synchronizing the illumination and imaging events and having those events be independently controlled relative to other events within the cycle as a fluid flow and hence microorganisms move through the viewing section 120. Accordingly, referring first to event "1" on the diagram of FIG. 11, there is simply shown a plot representing two cycles, each cycle being 33 ms at 30 FPS. Event #2 corresponds to initialization of the imager, which is indicated here as approximately 1.5 ms, starting from the beginning of the cycle. Event #3 is the imager illumination event, when whatever light(s) that are to illuminate the viewing port 144 are turned "on" so as to emit for a relatively brief period, here illustrated as approximately 3 ms or about ten percent (10%) or in the range of five to fifteen percent (5-15%) of the cycle, essentially broad spectrum or broadband light similar to bright sunlight (i.e., a "flash") so as to properly expose the image sensor. At event #4, substantially contemporaneous with the imager illumination event, is the image acquisition or "shutter" event, here indicated as approximately 2 ms—that is, the shutter event would begin just after and end just before the imager illumination event. It is also possible, depending on imaging system peculiarities, that this relationship could be reverse where the illumination event is shorter than the "shutter" event. After the image is acquired at event #4, event #5 represents the image data read or data download to the image processor or the like (not shown), which may take from 5-12 ms or more, depending on a number of factors, starting with the amount of data acquired and many other factors beyond the scope of the present invention (in FIG. 11 event #5 is represented as approximately 5 ms). Preferably, the image data read event is as short as possible simply to allow as much time for the data processing event (not shown on diagram) before the next cycle begins and a new set of image data is acquired. At event #6, more about which is said below, which runs from essentially the end of the image acquisition event #4 to the start of the next cycle, microorganisms in the fluid flow substantially within the viewing section 120 may be subject to one or more forms of stimulation during this time, here represented as an exemplary "wavelength stimulator" or stimulation from a particular spectrum of light energy, whether continuous or pulsed. Notably, such stimulation would have an effective "duty cycle" of approximately eighty to ninety percent (80-90%), or would represent approximately 26-29 ms of the nominal 33 ms exemplary cycle. During this period the organisms may experience "calm darkness" or other forms of stimulation other than light, or may be exposed to light stimulation distinct from the relatively instantaneous imager illumination light source having a duration of approximately 3 ms, which short duration event (event #3) the organisms would likely not respond to. But in terms of light stimulation during event #6 shown in the timing diagram of FIG. 11, for example, the stimulation means may be particular wavelengths of light such as a narrow color spectrum light. The source of such light may be similar LEDs as provided within the illumination ports 148 emitting a single or different wavelength(s), significantly different LEDs also positioned within the same illumination ports 148, or different LEDs positioned elsewhere within the viewing section 120, as will be appreciated particularly with respect to the alternative embodiments shown in FIGS. 15 and 16 and in FIGS. 17-19, discussed further below. Again, an important aspect of this "illumination synchronization" is that the illumination for the imager be independently controlled relative to any other illumination, which not only again provides the benefit of a relatively substantial "duty cycle" for such stimulation, as noted above, and thus the improved inducement of motion, but also improved detection of motion by isolating the imaging illumination and acquisition events effectively from everything else. That is, any colored light turned "on" during event #6 could be "off" during the imager events #s 2-4; however, it will again be appreciated that based on the location of any stimulation light source and the color (wavelength) and intensity of that light, it may simply be left on constantly as not interfering with or in any way adversely affecting the imaging illumination. Alternatively, irrespective of the illumination stimulation duty cycle and the type and capability of the lighting units, any such stimulation light source(s) may be strobed at a particular frequency rather than left on during all or part of the cycle in order to enhance stimulation for particular organisms. Those skilled in the art will further appreciate that a related benefit of such illumination synchronization capabilities within the system is that photosynthesis may be both caused and detected as a byproduct of such independent lighting control. Those skilled in the art will appreciate that the photosynthesis process in plants absorbs particular spectrum(s) of light energy. The standard detection process is to emit the spectrum(s) of light absorbed and detect the reduction of this energy that is reflected back. According to aspects of the present invention, independent control and synchronization of the imaging, stimulation, and plant life illumination can enhance the optimization of the measurement of chlorophyll levels (photosynthesis) and the other imaging related elements, providing yet another valuable data set in the sample analysis. For example, plants tend to absorb the non-green spectrums, while zooplankton (animals) tend to be attracted to the green spectrum because this is their "food"; thus, photosynthesis might be better detected with a blue emitter while zooplankton might be better attracted to a green emitter. With independent lighting control and the potential for multiple light sources and varied illumination durations, all such "stimulation" is possible.

By way of further example, and with continued reference to FIG. 11, another exemplary stimulation is pheromone stimulation, or the intermittent emission of pheromones into the fluid flow from a source (not shown) somewhere in or about the viewing section 120. That is, the idea is to provide controlled emission of micro-liters of semiochemicals (biosignals) into the viewing port 144 in order to excite a motile response from an organism such as zooplankton. Such pheromones may be any natural or synthetic products now known or later developed or discovered that can be shown to induce a motile response in a representative microorganism. In one exemplary embodiment, the pheromone micro-emitter would be positioned substantially in or near the viewing section body inlet 124 (FIG. 8) so as to attract a microorganism as it drifts through the viewing port 144 and goes out the outlet chute 182. As shown in connection with event #7, it is contemplated that the pheromone emission will be at some interval less than once per cycle—perhaps every 8th cycle (3 Hz), for example. The emission duration might be relatively short, generating "drops" of stimulant. Per the diagram, once emitted, the pheromones will "drift" through one or more cycles within the viewing section 120, such as over a period of 50 to 100 ms or longer, as compared with the exemplary approximately 33 ms cycle, but the actual, discrete pheromone emission event will be relatively less frequent and substantially instantaneous. Notably, the pheromone emission will not be initiated during imaging event #s 2-4, again, so as to not in any way interfere with or compromise the image acquisition. It will of course be appreciated that any such pheromone stimulation or other such non-illumination stimulation is entirely optional but may in certain contexts provide a complimentary source of stimulation. Finally in terms of the timing diagram of FIG. 11, event #8, shown on the same graph with event #3, again effectively represents the periods of time between imaging events #s 2-4 when an organism can simply "swim" undisturbed or be subjected to other forms of sensory or other stimulation. By way of further example regarding the kinds of stimulation to which organisms may be subjected substantially within the viewing section 120, localized relatively low-energy vibration stimulation or possibly acoustic stimulation are also contemplated. Either such device (see the exemplary vibratory stimulation device 250 of FIGS. 12-16) may again be located substantially near or in the entrance to the viewing port 144, such as in the viewing section body inlet 124 (FIG. 8), so as to excite or induce a "flight" response in an organism such as zooplankton, which will encourage such an organism to "flee" and "escape" with the flow through and out of the viewing section 120. The viewing section body outlet 146 and the outlet chute 182 itself will seem an "inviting" place for the organisms to retreat to. In the case of vibration stimulation, it may be located at or near the entrance of the proximity stimulator 240 (discussed below in connection with the alternative embodiment of FIGS. 12-16), and any such device would preferably be mechanically isolated from the rest of the viewing section 120. The idea is that this disturbance would not significantly propagate much beyond the location of emission. Similarly, some form of acoustic stimulation designed to excite the same "flight" response as the vibration stimulator may again be positioned substantially at or near the entrance to the viewing section 120. Such an acoustic stimulator would be based on acoustic tuning to provide a sense of appropriate distance and disturbance so as to again encourage the organisms to move towards the outlet chute 182. And as with the vibration stimulation, the acoustic stimulation device would also preferably be mechanically isolated from the rest of the viewing section 120 in order to optimize localization and effectiveness.

Figure 12:
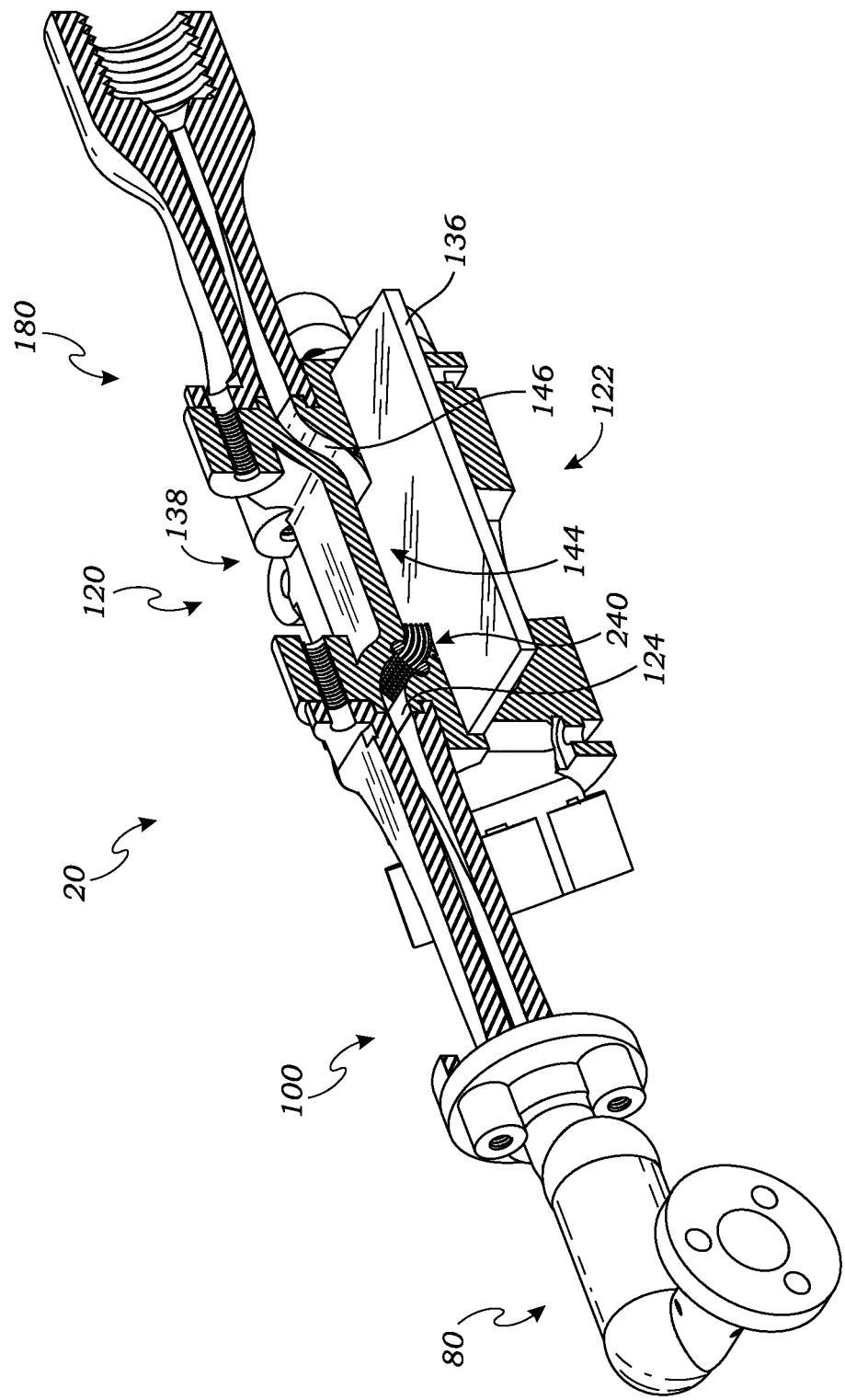
FIG. 12 is an enlarged partial sectional view of a third exemplary viewing section thereof, in accordance with at least one embodiment.
Figure 13:
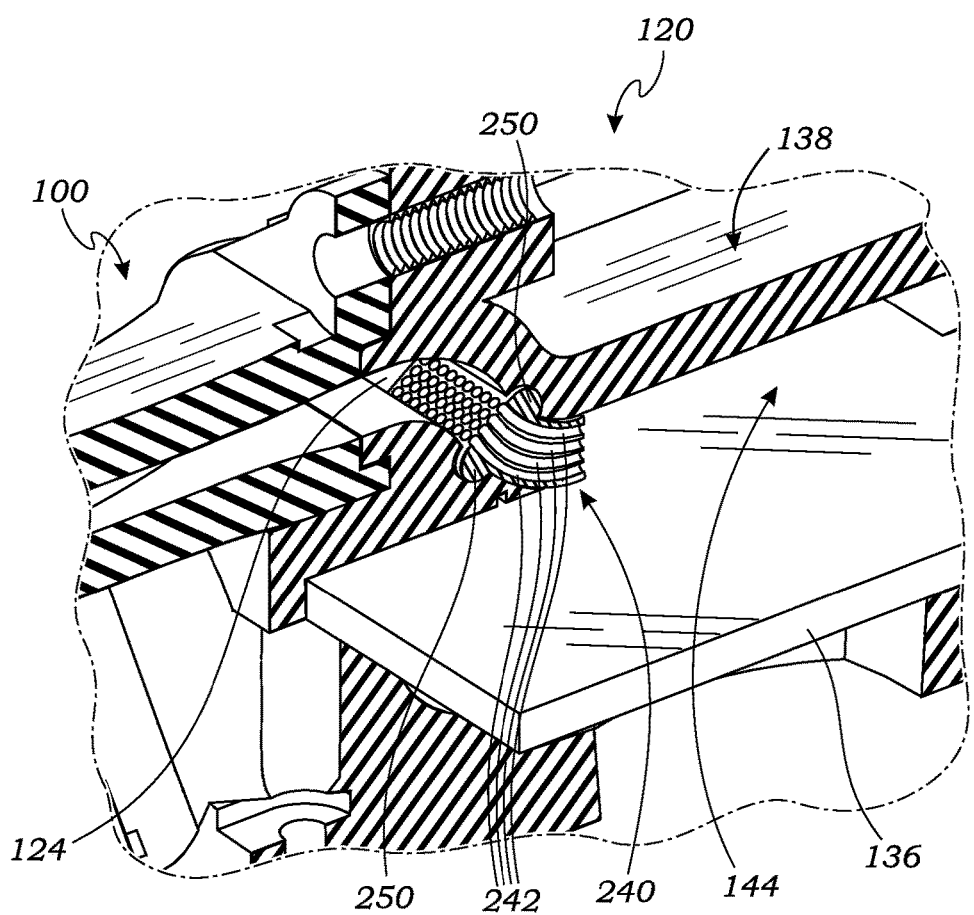
FIG. 13 is a further enlarged partial sectional view of the exemplary viewing section of FIG. 12.

Referring now to FIGS. 12-16, there are shown enlarged partial sectional views of the secondary, relatively smaller line of the exemplary dual sampling microorganism evaluation system 20 that samples from the main line shown in FIGS. 3-6, analogous to that of FIGS. 7-10 and so again generally comprising the stimulation section 80, the flow normalizing section 100, the viewing section 120, and the outlet section 180, only now including as alternative embodiments one or more further exemplary stimulation devices incorporated within the viewing section 120 thereof. First, as shown in FIGS. 12 and 13, there may be positioned within the viewing section body inlet 124 a proximity stimulation device 240, here shown as what is effectively a plug formed with numerous substantially parallel through-holes or sub-chutes 242 effectively communicating between the inlet 124 and the viewing port 144 within the viewing section 120. The idea is that the zooplankton or other organisms will sense the close proximity of the tunnel walls, or will feel a bit "claustrophobic" within the relatively smaller openings of the sub-chutes 242 and will provide or exhibit a motile response when entering the "tranquil" and "wide open" waters of the viewing port 144. It will be appreciated by those skilled in the art that a virtually infinite variety of shapes, sizes and configurations of any such proximity stimulation device 240, and its location, are possible without departing from the spirit and scope of the present invention. As also shown in FIGS. 12 and 13, a vibratory stimulation device 250 may also be positioned in or adjacent to or integrated within the viewing section body inlet 124 to further stimulate organisms passing into and through the inlet 124, with or without the proximity stimulation device 240; but where a proximity stimulation device 240 is employed, as shown, it would be preferable to locate such a vibratory stimulation device 250, an acoustic stimulation device, or other such stimulation device closer to the entrance of the inlet 124 or of the device 240 itself so as to again elicit the "flight" response of the organisms and encourage them to rush down through the chute(s) and into the "calmer waters" of the viewing section viewing port 144, where their motile responses would be observed. Briefly, as shown in FIG. 14, the proximity stimulation device 240 may be employed within the viewing section body inlet 124 alone, without the vibratory stimulation device 250 (FIGS. 12 and 13); again, any such combination of stimulation means and mechanisms is possible in the present invention without departing from its spirit and scope. Furthermore, as shown in FIG. 14, the basic upstream microorganism stimulation section 80 is shown in section as well, revealing portions of the one or more disorientation spiral loops 84, 88 formed therein.

Figure 15:
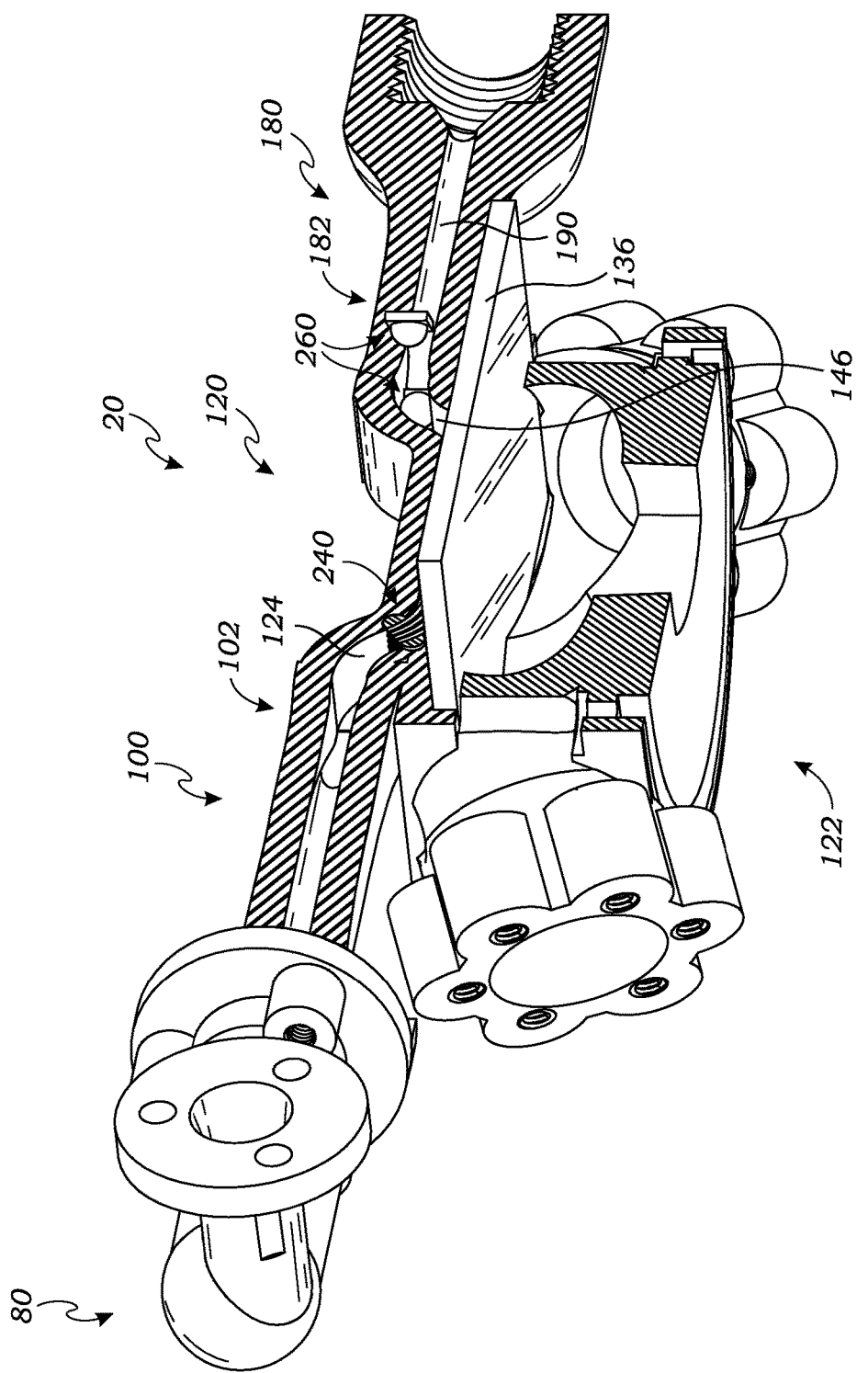
FIG. 15 is an enlarged partial sectional view of a fourth exemplary viewing section thereof.
Figure 16:
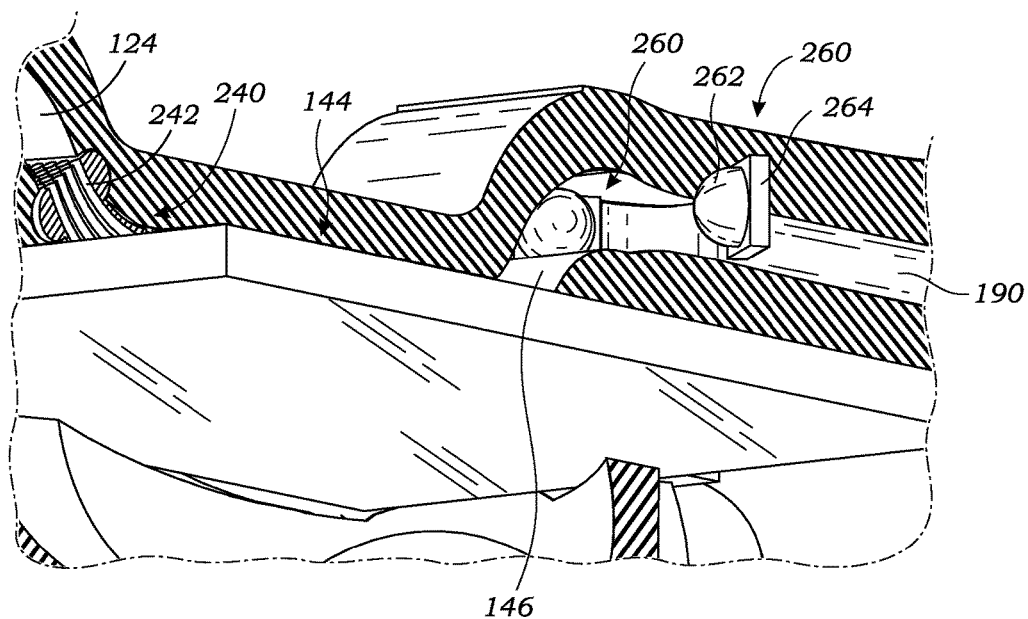
FIG. 16 is a further enlarged partial sectional view of the exemplary viewing section of FIG. 15.

Turning to FIGS. 15 and 16, there are shown enlarged partial sectional views of particularly the viewing section 120 now including a still further exemplary stimulation device in the form of one or more light sources 260 positioned here within or substantially near the exit of the viewing section body outlet 146 so as to draw or attract organisms thereto. Particularly, there is shown in the exemplary embodiment two offset light stimulation devices 260 substantially at the exit of the viewing section body outlet 146 or the entrance to the outlet chute inner bore 190, spaced on either side thereof and so positioned as to draw organisms in the viewing port 144 up and out of the viewing section 120 through the outlet 146. The idea is to essentially place a narrow spectrum emitter of some kind in or adjacent the outlet chute 146 of the viewing section 120 that is giving off light that the organisms like and will swim towards. In that regard, it has been discovered that zooplankton, for example, has light receptors that would appear to be optimized for performance relative to the color of their food (phytoplankton) and the light filtering characteristics of water. It is of significant note that wavelengths of approximately 530 nm (green) appear to be effective in attracting zooplankton particularly, though other wavelengths such as approximately 475 nm (blue) may also be effective, such that the invention is expressly not limited to a particular wavelength or color of light in this context; it will be appreciated that different organisms may be attracted to or prefer different colors of light. Any such light stimulation will generally be most effective when there are not other competing wavelengths in proximity, which again relates back to the above illumination synchronization discussion and the idea that not only is there to be no light interference with the light stimulation devices 260, but there is also to be no interference by such devices 260 with the imager events #s 2-4 in FIG. 11; as such, again, there is benefit in having the imager light source(s) and the stimulation light source(s) independently controlled as herein disclosed. Back to the placement of the light stimulation devices 260 substantially at the exit of the viewing section body outlet 146, or "up the ramp," it will be appreciated that such placement draws the organisms further up the exit and allows for emission of relatively soft light cascading or filtering down into the viewing port 144 even when "on" during the non-image acquisition phase of the cycle, thereby also rendering less likely any light "pollution" within the viewing port 144 during image acquisition in the event the stimulation or attraction lights 260 were even to be "on". Relatedly, as shown, the exemplary light stimulation devices 260 have domed, semi-spherical lenses 262 that more readily diffuse light from the LED or other light source therebeneath (not shown). In other contexts a "point" light versus a diffused light might be preferable. Each such light source and lens 262 is shown as being mounted on a base 264, though it will be appreciated that each such light stimulation device 260 may be integrated into or mounted in the viewing section body 122 or the outlet chute 182 in virtually any manner now known or later developed for securing and positioning such light stimulation devices 260 as desired. Again, it will be further appreciated that a variety of number, configuration and location of such devices 260 are possible without departing from the spirit and scope of the invention. By way of further example and illustration, the inlet and outlet chutes 102 may be different geometries in order to support "line of sight" to the emitter once the zooplankton or other organisms enter the viewing chamber 144. Or, any such devices 260 may simply be placed nearer to or even in the exit area 146 of the viewing section 120 instead (see, for example, the alternative embodiment shown in FIG. 19 discussed immediately below).

Figure 17:
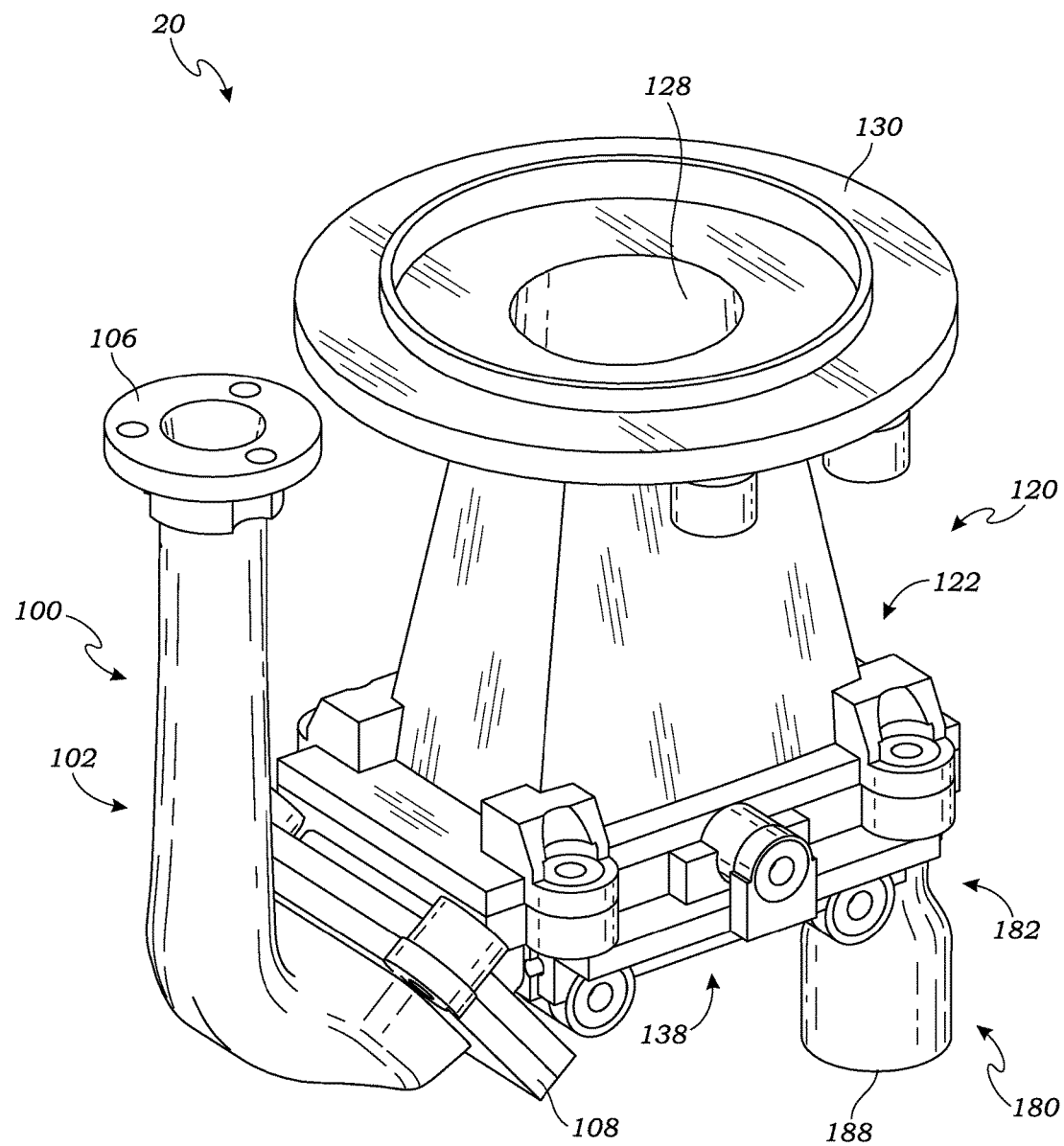
FIG. 17 is an enlarged partial perspective view of a fifth exemplary viewing section thereof, in accordance with at least one embodiment.
Figure 18:
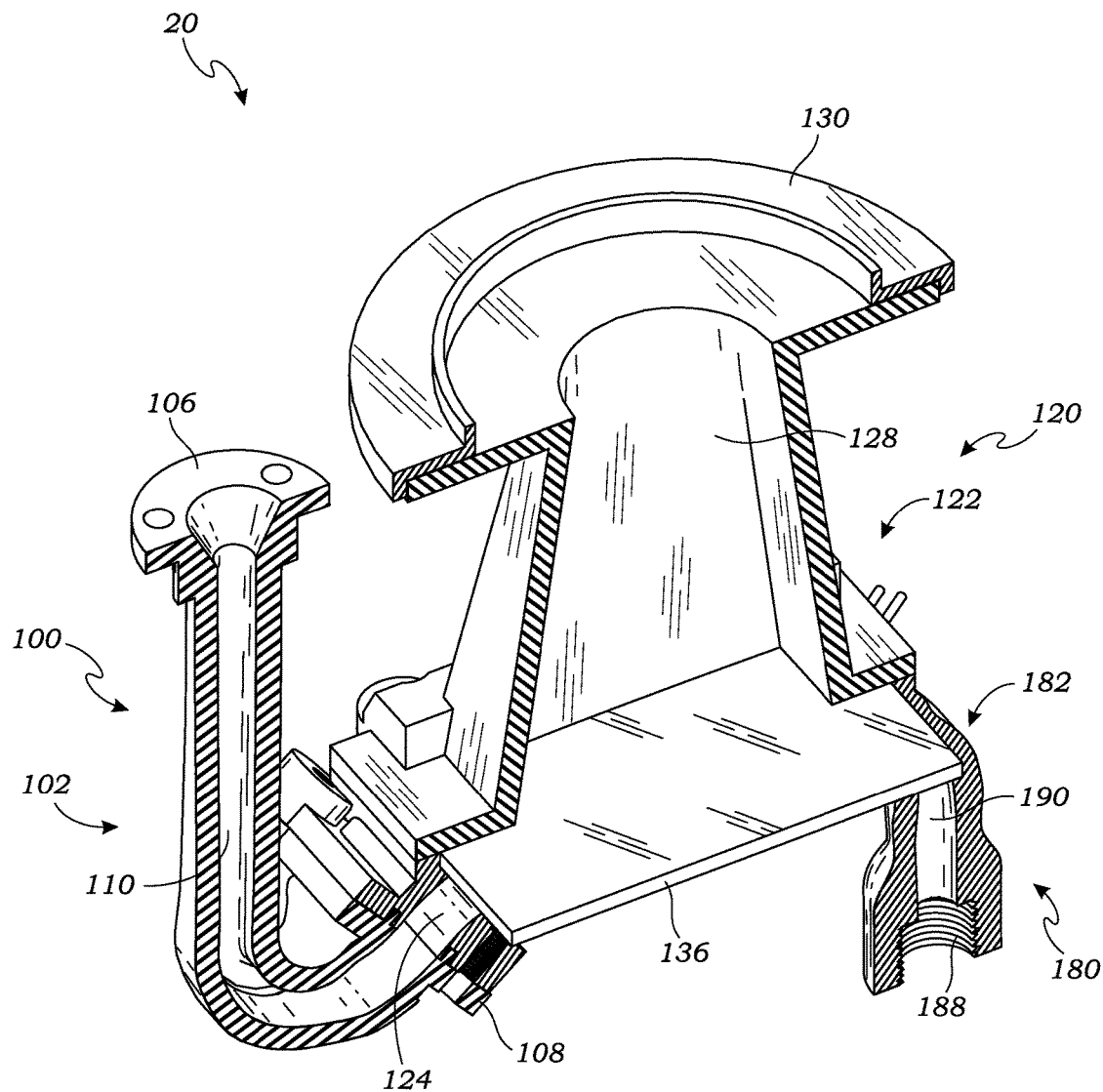
FIG. 18 is a partial sectional view of the exemplary viewing section of FIG. 17 taken from a first perspective.
Figure 19:
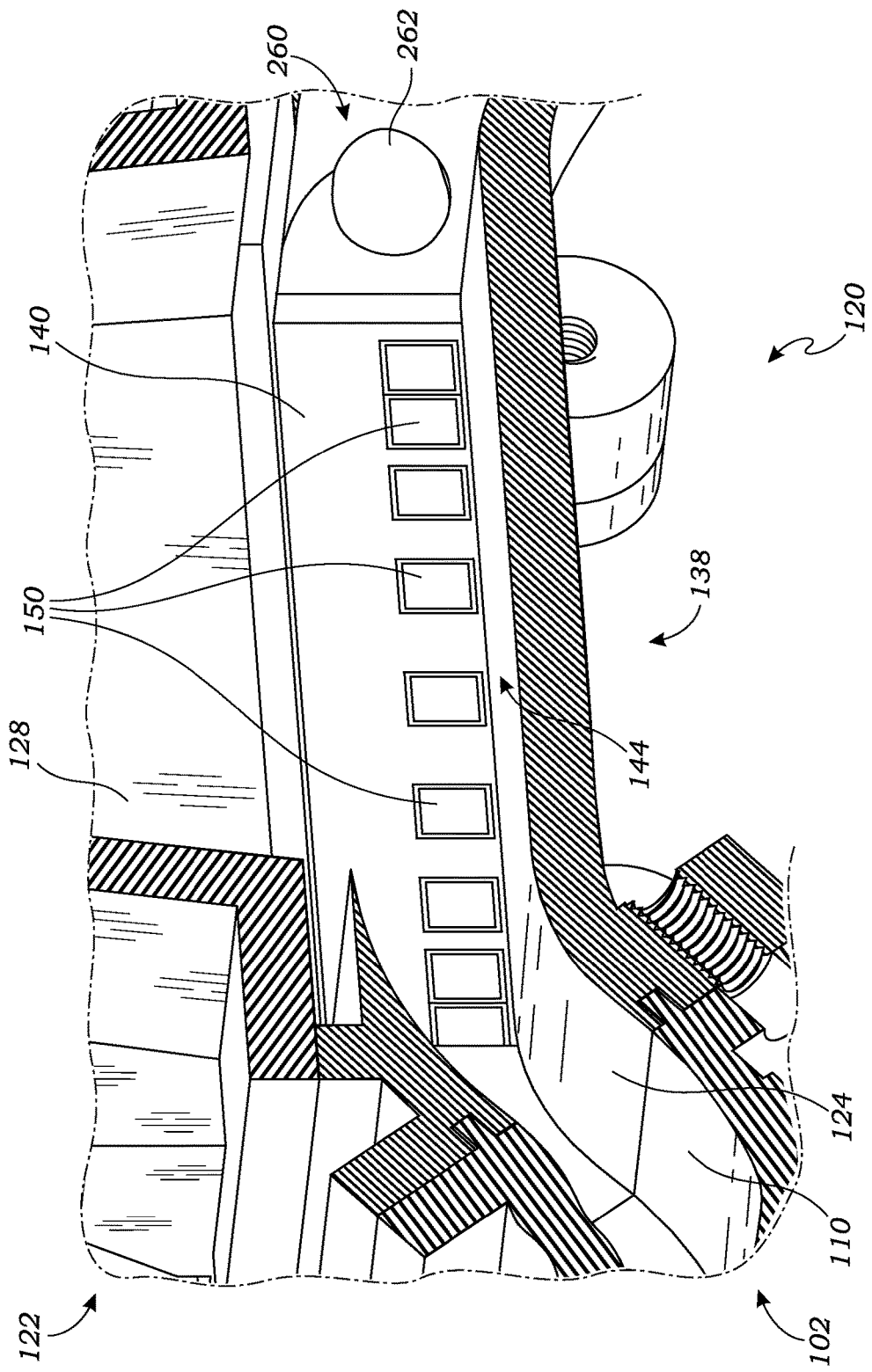
FIG. 19 is an enlarged partial sectional view of the exemplary viewing section of FIG. 17 taken from a second perspective.

Finally, referring now to FIGS. 17-19, there is shown yet another exemplary embodiment of a microorganism evaluation system 20 according to further aspects of the present invention, particularly once more in connection with the viewing section 120. As can be first observed from the perspective view of FIG. 17, taken from a vantage point looking somewhat down at the optical system mount 130 (more like FIGS. 1-3 versus FIGS. 4-6), the inlet section 100 and outlet section 180 are oriented essentially perpendicular to the viewing section 120 rather than substantially parallel as in the other illustrated embodiments. It will again be appreciated generally that any and all such orientations are possible within the present invention without departing from its spirit and scope. Here, it will be appreciated that such a change in orientation of the inlet and outlet sections 100, 180 may be for reasons of flow considerations or simply spatial or "packaging" constraints. In any case, as best seen in FIG. 18, the exit of the inlet chute 102 and particularly its inner bore 110 in the vicinity of the distal coupling 108 is yet configured to substantially seamlessly and sealingly engage, join, or otherwise flow into the viewing section body inlet 124 when the components are installed together; a similar arrangement would be true of the outlet chute 182. As also shown in FIG. 18, once again a clear or substantially transparent viewing plate 136 is positioned within the viewing section 120 assembly so as to effectively form one of the four sides of the conduit or flow path defining the viewing port 144 (FIG. 19). Here, the viewing plate 136 is configured to seat or be mounted and secured between the viewing section body 122 and the back plate 138. Though not shown, it will be appreciated from the foregoing that a proximity stimulator 240 and/or vibratory stimulation device 250 (FIG. 13) or other such device may be placed within the viewing section body inlet 124 as well. Other features and aspects as shown in other exemplary embodiments herein or as otherwise consistent with or contemplated by the present disclosure may thus be incorporated within the viewing section 120 or other components of the system 20. Turning to FIG. 19, an enlarged sectional view of the viewing section 120 taken more from the side (and with the viewing plate 136 removed for simplicity), there is best shown the interior features of the exemplary device, and particularly the region of the viewing port 144. Notably, there are shown a series of imaging light sources 150 operably installed in a lengthwise side wall 140 here of the back plate 138 though more generally within the viewing section 120 and more particularly the viewing port 144. Though not shown, it will be appreciated that a similar bank of imaging light sources 150 could also be provided on the opposite side of the viewing port 144 for illumination from both sides. In any case, such imaging light sources 150 may be LEDs or any other such technology as now known or later developed in the art, here shown as being contained within the viewing section 120, or incorporated or installed within a wall thereof, such that no separate illumination ports 148 (FIG. 7) in which would be installed illumination LEDs are shown or required, though those skilled in the art will appreciate that such light sources at an angle may still be employed in addition to the side-mounted imaging LEDs 150 shown in FIG. 19. Fundamentally, side illumination light source(s) as with the imaging LEDs 150 may have a number of advantages in terms of image acquisition and quality. First, such an installation and method mitigates the development of shadows from microorganisms moving about in the viewing port 144, which shadows would tend to be cancelled out by the opposing illumination emitters 150. The arrangement also potentially increases the imaging contrast developed by the microorganisms within the flow in the viewing port 144, as the surface on the body of the microorganism that is closest to the imager will tend to be darker than the side of the microorganism that is illuminated, since the imaging equipment (not shown) is mounted on the optical system mount 130 (FIGS. 17 and 18) well above the plane of the imaging LEDs 150. Relatedly, the side-mounted LEDs 150 also mitigate the potential for light energy to be reflected into the imager, including reflections from the various surfaces found within the viewing section's cavity opening 128, or the space between the viewing port 144 and the imager (not shown) that would be mounted above. In fact, by having the imager separated from the viewing port 144 and emitters 150 by the clear viewing plate 136 (FIG. 18), light will not bounce off of the glass or similar material because the illumination is contained in the fluid underneath the viewing plate 136. With further reference to FIG. 19, each imaging light source 150 is shown somewhat nondescriptly as a rectangular configuration LED flush mounted with the side wall 140. It will be appreciated by those skilled in the art that any shape or lens configuration or angle or again more generally any illumination technology now known or later developed may be employed. It is here contemplated that the one or more side-mounted imaging LEDs 150 would have relatively wide angle lenses so as to enhance the emission of relatively more uniform spatial distribution of light energy, which should generate a relatively "flat" and uniform background, as further aided by the inherent diffusing nature of the fluid itself within the viewing port 144. While the bank of imaging LEDs 150 on a particular side of the viewing section 120 may be spaced uniformly, as shown in FIG. 19, by design, the imaging LEDs 150 are closer together at the marginal edges of the viewing port 144 or at the respective left and right or inlet and outlet edges of the side wall 140. Toward the center of the viewing port 144 it would tend to be brightest, where the light from effectively more imaging LEDs 150 would be compounded or aggregated, while toward the marginal edges where there are relatively fewer LEDs 150 to contribute to the illumination, it would tend to be relatively darker. Thus, by having a higher density or concentration, via closer spacing, of light sources at the margins, the net effect is substantially uniform or even lighting of the entire viewing port 144. The specific sizes and spacing of the imaging LEDs 150 and their number per side (nine shown in FIG. 19), are not to be taken literally or to scale or to be in any way limiting, it being appreciated that FIG. 19 and the related discussion is merely illustrative of features and aspects of the invention. Accordingly, a wide variety of other configurations and arrangements of imaging light sources, again, whether for side or angled or direct illumination or any combination thereof, are to be understood as within the spirit and scope of the invention. As also shown in FIG. 19, at least one stimulation light source 260 having a lens 262 may be positioned substantially at the exit of the viewing port 144 or of the viewing section 120 more generally so as to attract or stimulate microorganisms within the flow as above-described. As also described herein, the operation of such attractant light source 260 may be synchronized with any imaging light source 150 in the viewing section 120 depending on a variety of factors. Those skilled in the art will again appreciate that a variety of lighting arrangements and control are possible without departing from the spirit and scope of the present invention.

Aspects of the present specification may also be described as follows:

1. A microorganism evaluation system comprising a viewing section for image acquisition, the viewing section comprising: a viewing port configured to accommodate a fluid flow from a viewing section body inlet to a viewing section body outlet; at least one independently controlled imaging light source operably installed in the viewing section and configured to selectively illuminate the viewing port; and at least one independently controlled light stimulation device operably installed in the viewing section and configured to selectively emit light for invoking a motile response in a microorganism within the fluid flow in the viewing port, whereby the system synchronizes illumination of the at least one imaging light source and the at least one light stimulation device of the viewing section.

2. The system of embodiment 1 wherein the viewing section further comprises: a viewing section body; and a back plate, the viewing section body and the back plate together defining the viewing port.

3. The system of embodiment 2 wherein: the viewing section body is formed with at least one illumination port configured to optically communicate with the viewing port; and the at least one imaging light source is located in the at least one illumination port.

4. The system of embodiment 2 wherein the at least one imaging light source is installed in the viewing section body.

5. The system of embodiment 2 wherein the at least one imaging light source is installed in the back plate.

6. The system of embodiment 2 wherein a viewing plate is installed within the viewing section substantially opposite the back plate, between the back plate and an optical system cavity opening formed in the viewing section body and configured to optically communicate with the viewing port, the viewing plate being substantially transparent; and the at least one imaging light source is installed in the viewing section so as to be bounded by the back plate and the viewing plate and thus positioned within the viewing port.

7. The system of embodiment 1 wherein the at least one imaging light source is installed in the viewing section so as to provide substantially side illumination within the viewing port.

8. The system of embodiment 7 wherein a plurality of imaging light sources are aligned as an array within the viewing port.

9. The system of embodiment 8 wherein the plurality of imaging light sources are unequally spaced, with a higher density of imaging light sources at the margins of the viewing port.

10. The system of embodiment 8 wherein the plurality of imaging light sources are LEDs.

11. The system of embodiment 1 wherein the at least one light stimulation device is operably installed in the viewing section body outlet.

12. The system of embodiment 1 wherein: an outlet chute is installed on the viewing section so as to be in fluid communication with the viewing port by way of the viewing section body outlet; and the at least one light stimulation device is operably installed in the outlet chute.

13. The system of embodiment 1 wherein the at least one light stimulation device is configured to emit light having a wavelength of approximately 530 nm (green).

14. The system of embodiment 1 wherein the at least one light stimulation device is operated continuously.

15. The system of embodiment 1 wherein the at least one light stimulation device is pulsed.

16. The system of embodiment 1 wherein the at least one imaging light source and the at least one light stimulation device are co-located.

17. The system of embodiment 1 wherein the viewing section further comprises a vibratory stimulation device.

18. The system of embodiment 17 wherein the vibratory stimulation device is operably installed in the viewing section body inlet.

19. The system of embodiment 17 wherein: an inlet chute is installed on the viewing section so as to be in fluid communication with the viewing port by way of the viewing section body inlet; and the vibratory stimulation device is operably installed in the inlet chute.

20. The system of embodiment 1 wherein the viewing section further comprises a proximity stimulation device.

21. The system of embodiment 20 wherein the proximity stimulation device is configured as a plug formed with a plurality of substantially parallel sub-chutes.

22. The system of embodiment 21 wherein: an inlet chute is installed on the viewing section so as to be in fluid communication with the viewing port by way of the viewing section body inlet; and the proximity stimulation device is operably installed in the viewing section body inlet so as to be in fluid communication between the inlet chute and the viewing port within the viewing section by way of the plurality sub-chutes.

23. The system of embodiment 21 wherein: an inlet chute is installed on the viewing section so as to be in fluid communication with the viewing port by way of the viewing section body inlet; and the proximity stimulation device is operably installed in the inlet chute so as to be in fluid communication with the viewing section body inlet by way of the plurality sub-chutes.

24. The system of embodiment 1 further comprising a microorganism stimulation mechanism selected from the group consisting of acoustic energy and pheromones.

25. The system of embodiment 1 wherein: a cycle of the system is defined as the time period from the start of one discrete illumination event of the at least one imaging light source to the next; and each imaging light source illumination event represents approximately five to fifteen percent (5-15%) of the cycle.

26. The system of embodiment 25 wherein the cycle is approximately fifteen to forty-five milliseconds (15-45 ms).

27. The system of embodiment 25 wherein the illumination event of the at least one light stimulation device represents approximately eighty to ninety percent (80-90%) of the cycle.

28. The system of embodiment 25 wherein the illumination event of the at least one light stimulation device represents approximately eighty to one-hundred percent (80-100%) of the cycle.

29. The system of embodiment 1 wherein: a first illumination event is associated with operation of the at least one imaging light source; a second illumination event is associated with operation of the at least one light stimulation device; and the first and second events are substantially non-overlapping.

30. A microorganism evaluation system comprising a viewing section for image acquisition, the viewing section comprising: a viewing port in visual communication with an optical system cavity opening formed in the viewing section, the viewing port configured to accommodate a fluid flow; a plurality of imaging light sources operably installed within the viewing port so as to provide substantially side illumination therein; and at least one independently controlled light stimulation device operably installed in the viewing section and configured to selectively emit light for invoking a motile response in a microorganism within the fluid flow in the viewing port, whereby the system synchronizes illumination of the plurality of imaging light sources and the at least one light stimulation device of the viewing section.

31. A method of operating a viewing section of a microorganism evaluation system, comprising the steps of: activating an independently controlled imaging light source operably installed in the viewing section and configured to selectively illuminate a viewing port thereof, the viewing port configured to accommodate a fluid flow; and activating an independently controlled light stimulation device operably installed in the viewing section and configured to selectively emit light for invoking a motile response in a microorganism within the fluid flow in the viewing port.

32. The method of embodiment 31 wherein prior to the step of activating the independently controlled light stimulation device, the method comprises the further step of deactivating the imaging light source.

33. The method of embodiment 32 wherein the time the imaging light source is activated represents approximately five to fifteen percent (5-15%) of the total time from one imaging light source activation event to the next, which total time defines a cycle of the system.

34. The method of embodiment 33 comprising the further step of deactivating the light stimulation device prior to activating the imaging light source a subsequent time, wherein no imaging light source activation event and light stimulation device activation event overlap.

35. The method of embodiment 34 wherein the light stimulation device activation event represents approximately eighty to ninety percent (80-90%) of the cycle.

36. The method of embodiment 31 wherein the light stimulation device activation event represents approximately eighty to one-hundred percent (80-100%) of a cycle of the system defined as the total time from one imaging light source activation event to the next.

37. The method of embodiment 31 wherein the steps of activating the independently controlled imaging light source and activating the independently controlled light stimulation device are synchronized.

38. The method of embodiment 37 wherein the steps of activating the independently controlled imaging light source and activating the independently controlled light stimulation device overlap.

39. The method of embodiment 31 wherein the step of activating the independently controlled light stimulation device entails emission of narrow spectrum light.

40. The method of embodiment 32 wherein the step of emitting narrow spectrum light further entails pulsing the light stimulation device.

41. The method of embodiment 31 comprising the further step of operating an image acquisition shutter at least partially during the imaging light source activation event.

42. The method of embodiment 41 wherein the step of operating the image acquisition shutter occurs entirely during the imaging light source activation event.

43. The method of embodiment 31 comprising the further step of emitting drops of pheromones into the fluid flow.

44. The method of embodiment 31 comprising the further step of introducing acoustic energy into the fluid flow.

45. The method of embodiment 31 comprising the further step of introducing vibrations into the fluid flow.

46. The method of embodiment 31 comprising the further step of passing the fluid flow through a proximity stimulation device having a plurality of substantially parallel sub-chutes.

To summarize, regarding the exemplary embodiments of the present invention as shown and described herein, it will be appreciated that a microorganism evaluation system, particularly a viewing section thereof, is disclosed and configured for both stimulating and acquiring images of microorganisms within a fluid, including aspects related to synchronizing the various illumination events within the system. Because the principles of the invention may be practiced in a number of configurations beyond those shown and described, it is to be understood that the invention is not in any way limited by the exemplary embodiments, but is generally able to take numerous forms in doing so without departing from the spirit and scope of the invention.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be expressly understood that the disclosed subject matter is in no way limited to a particular apparatus, methodology, configuration, size, shape, material of construction, protocol, etc., described herein, but may include any such technology now known or later developed without departing from the spirit and scope of the specification. Furthermore, the various features of each of the above-described embodiments may be combined in any logical manner and are intended to be included within the scope of the present invention. As such, various modifications or changes to or alternative configurations of the disclosed subject matter can be made in accordance with the teachings herein without departing from the spirit and scope of the present specification. Lastly, the terminology used herein is for the purpose of describing particular embodiments only, and is not intended to limit the scope of the present invention. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor believes that the claimed subject matter is the invention.

What is claimed is:

1. A microorganism evaluation system comprising a viewing section for image acquisition, the viewing section comprising:
   a viewing section body inlet and an opposite viewing section body outlet and a viewing port therebetween, the viewing port configured to accommodate a fluid flow therethrough from the viewing section body inlet to and out of the viewing section body outlet;
   imaging equipment operably installed on the viewing section adjacent to the viewing port;
   at least one independently controlled imaging light source operably installed in the viewing section and configured to selectively illuminate the viewing port; and
   at least one independently controlled light stimulation device operably installed in the viewing section and configured to selectively emit visible light for invoking a motile response in a microorganism within the fluid flow in the viewing port, whereby the system allows for continuous viewing section flow throughput and synchronizes illumination of the at least one imaging light source and the at least one light stimulation device of the viewing section for improved image acquisition by the imaging equipment.

2. The system of claim 1 wherein the viewing section further comprises:
   a viewing section body; and
   a back plate, the viewing section body and the back plate together defining the viewing port.

3. The system of claim 2 wherein:
   a viewing plate is installed within the viewing section substantially opposite the back plate, between the back plate and an optical system cavity opening formed in the viewing section body and configured to optically communicate with the viewing port, the viewing plate being substantially transparent, the imaging equipment optically communicating with the optical system cavity opening and thus with the viewing port through the viewing plate; and
   the at least one imaging light source is installed in the viewing section so as to be bounded by the back plate and the viewing plate and thus positioned within the viewing port.

4. The system of claim 1 wherein the at least one imaging light source is installed in the viewing section so as to provide substantially side illumination within the viewing port.

5. The system of claim 4 wherein a plurality of imaging light sources are aligned as an array within the viewing port.

6. The system of claim 1 wherein the at least one light stimulation device is operably installed in the viewing section body outlet.

7. The system of claim 1 wherein:
   an outlet chute is installed on the viewing section so as to be in fluid communication with the viewing port by way of the viewing section body outlet; and
   the at least one light stimulation device is operably installed in the outlet chute.

8. The system of claim 1 wherein the at least one light stimulation device is configured to emit light having a wavelength of approximately 530 nm (green).

9. The system of claim 1 wherein the at least one imaging light source and the at least one light stimulation device are co-located.

10. The system of claim 1 wherein the viewing section further comprises a vibratory stimulation device.

11. The system of claim 1 wherein the viewing section further comprises a proximity stimulation device.

12. The system of claim 11 wherein the proximity stimulation device is configured as a plug formed with a plurality of substantially parallel sub-chutes.

13. The system of claim 12 wherein:
   an inlet chute is installed on the viewing section so as to be in fluid communication with the viewing port by way of the viewing section body inlet; and
   the proximity stimulation device is operably installed in the viewing section body inlet so as to be in fluid communication between the inlet chute and the viewing port within the viewing section by way of the plurality of sub-chutes.

14. The system of claim 1 further comprising a microorganism stimulation mechanism selected from the group consisting of acoustic energy and pheromones.

15. A microorganism evaluation system comprising a viewing section for image acquisition, the viewing section comprising:
   a viewing port in visual communication with an optical system cavity opening formed in the viewing section, the viewing port configured to accommodate a fluid flow through the viewing port;
   imaging equipment operably installed on the viewing section adjacent to the viewing port in optical communication with the optical system cavity opening and thus with the viewing port;
   a plurality of imaging light sources operably installed within a side wall of the viewing port so as to provide substantially side illumination therein; and
   at least one independently controlled light stimulation device operably installed in the viewing section and configured to selectively emit light for invoking a motile response in a microorganism within the fluid flow in the viewing port, whereby the system allows for continuous viewing section flow throughput and synchronizes illumination of the plurality of imaging light sources and the at least one light stimulation device of the viewing section for improved image acquisition by the imaging equipment.

16. A method of illumination synchronization within a microorganism evaluation system comprising a viewing section for fluid flow therethrough and image acquisition, the method comprising:
   flowing a fluid through a viewing port from a viewing section body inlet to and out of a viewing section body outlet;
   independently controlling an at least one imaging light source operably installed in the viewing section to selectively illuminate the viewing port;
   independently controlling an at least one light stimulation device operably installed in the viewing section to selectively emit visible light for invoking a motile response in a microorganism within the fluid flow in the viewing port, whereby use of the system allows for continuous viewing section flow throughput and synchronizing illumination of the at least one imaging light source and the at least one light stimulation device of the viewing section for improved image acquisition, a cycle of the system being defined as the time period from the start of one discrete illumination event of the at least one imaging light source to the next; and
   acquiring an image of a microorganism during the cycle.

17. The method of claim 16 wherein the step of independently controlling an at least one imaging light source defines an imaging light source illumination event representing approximately five to fifteen percent (5-15%) of the cycle.

18. The method of claim 17 wherein the step of independently controlling an at least one light stimulation device defines a light stimulation device illumination event representing approximately eighty to one-hundred percent (80-100%) of the cycle.

19. The method of claim 16 wherein the cycle is approximately fifteen to forty-five milliseconds (15-45 ms).

20. The method of claim 16 wherein:
the step of independently controlling an at least one imaging light source defines a first illumination event associated with operation of the at least one imaging light source;
the step of independently controlling an at least one light stimulation device defines a second illumination event associated with operation of the at least one light stimulation device; and
the first and second illumination events are substantially non-overlapping.

\* \* \* \* \*